US011673955B2

(12) United States Patent
St. John

(10) Patent No.: US 11,673,955 B2
(45) Date of Patent: Jun. 13, 2023

(54) TARGETED PREVENTION OF MATERNAL TO FOETAL VERTICAL TRANSMISSION OF INFECTION

(71) Applicant: National University of Singapore, Singapore (SG)

(72) Inventor: Ashley St. John, Singapore (SG)

(73) Assignee: National University of Singapore, Singapore (SG)

( * ) Notice: Subject to any disclaimer, the term of this patent is extended or adjusted under 35 U.S.C. 154(b) by 17 days.

(21) Appl. No.: 16/612,221

(22) PCT Filed: May 10, 2018

(86) PCT No.: PCT/SG2018/050228
§ 371 (c)(1),
(2) Date: Nov. 8, 2019

(87) PCT Pub. No.: WO2018/208231
PCT Pub. Date: Nov. 15, 2018

(65) Prior Publication Data
US 2021/0115136 A1 Apr. 22, 2021

(30) Foreign Application Priority Data
May 11, 2017 (SG) .............................. 10201703861T

(51) Int. Cl.
*C07K 16/28* (2006.01)
*A61P 31/14* (2006.01)
*A61K 39/00* (2006.01)

(52) U.S. Cl.
CPC ............ *C07K 16/283* (2013.01); *A61P 31/14* (2018.01); *A61K 2039/505* (2013.01); *A61K 2039/55* (2013.01); *C07K 2317/20* (2013.01); *C07K 2317/21* (2013.01); *C07K 2317/24* (2013.01); *C07K 2317/34* (2013.01); *C07K 2317/622* (2013.01); *C07K 2317/76* (2013.01)

(58) Field of Classification Search
None
See application file for complete search history.

(56) References Cited

U.S. PATENT DOCUMENTS

| | | | | |
|---|---|---|---|---|
| 7,662,928 B2 * | 2/2010 | Balthasar | ............ | C07K 16/283 530/388.22 |
| 2007/0092507 A1 | 4/2007 | Balthasar et al. | | |

FOREIGN PATENT DOCUMENTS

| | | |
|---|---|---|
| WO | WO-2017/189891 | 11/2017 |
| WO | WO-2018/023136 | 2/2018 |

OTHER PUBLICATIONS

Zdravic et al., Seminars in Fetal & Neonatal Medicine, Feb. 2016, 21:19-27. (Year: 2016).*
Pattnaik et al., Vaccine, 2020, 8, 266, 19 pages. (Year: 2020).*
Maidji et al., "Maternal Antibodies Enhance or Prevent Cytomegalovirus Infection in the Placenta by Neonatal Fc Receptor-Mediated Transcytosis," Am. J. Pat., vol. 168, No. 4, pp. 1210-1226 (Apr. 2006).
Tsunoda et al., "Neuropathogenesis of Zika Virus Infection: Potential Roles of Antibody-Mediated Pathology," Author Manuscript, published in final edited form as: Acta Med. Kinki Univ., vol. 41, No. 2, pp. 37-52 (2016).
Low and Mezo, "Inhibitors of the FcRn:IgG Protein-Protein Interaction," AAPS J., vol. 11, No. 3, pp. 432-434 (Jun. 5, 2009).
Vaccaro et al., "Engineering the Fc region of immunoglobulin G to modulate in vivo antibody levels," Nat. Biotech., vol. 23, pp. 1283-1288 (Sep. 25, 2005).
Mezo et al., "Reduction of IgG in nonhuman primates by a peptide antagonist of the neonatal Fc receptor FcRn," Proc. Natl. Acad. Sci. USA, vol. 105, No. 7, pp. 2337-2342 (Feb. 12, 2008).
Wang et al., "Discovery and structure—activity relationships of small molecules that block the human immunoglobulin G—human neonatal Fc receptor (hIgG—hFcRn) protein-protein interaction," Bioorg. Med. Chem. Lett., vol. 23, No. 5, pp. 1253-1256 (Jan. 11, 2013).
Bardina et al., "Enhancement of Zika virus pathogenesis by preexisting antiflavivirus immunity," Author Manuscript, published in final edited form as: Science, vol. 356, No. 6334, pp. 175-180 (Apr. 14, 2017).
Paul et al., "Dengue virus antibodies enhance Zika virus infection," Clin. Transl. Immunology, vol. 5, No. 12, e117, pp. 1-9 (Dec. 16, 2016).
International Search Report and Written Opinion for International Patent Application No. PCT/SG2018/050228 dated Aug. 6, 2018 (13 pages).
Breitbach, et al., "Primary infection with dengue or Zika virus does not affect the severity of heterologous secondary infection in macaques", PLOS Pathogens, https://doi.org/10.1371/journal.ppat.1007766, Aug. 1, 2019, 28 pgs.
Delgado, et al., "Improved Immune Responses Against Zika Virus After Sequential Dengue and Zika Virus Infection in Human", MDPI viruses, www.mdpi.com/journal/viruses, 2018, 10, 480, 20 pgs.
Edlow, et al., "Assessment of Maternal and Neonatal SARS-CoV-2 Viral Load, Transplacental Antibody Transfer, and Placental Pathology in Pregnancies During the COVID-19 Pandemic", JAMA Network Open, Dec. 22, 2020, 17 pgs.

(Continued)

*Primary Examiner* — Stacy B Chen
(74) *Attorney, Agent, or Firm* — Mintz, Levin, Cohn, Ferris, Glovsky and Popeo, P.C.

(57) ABSTRACT

The present invention relates to targeted prevention of vertical transmission of infection between mother and foetus. More particularly, the invention relates to methods of preventing neonatal Fc receptor (FcRn)-mediated transmission of virus, preferably flavivirus, more preferably Zika virus (ZIKV), from a mother immune to a cross-reactive virus e.g. Dengue virus (DENY) to her foetus, and to reagents that block or inhibit said FcRN-mediated transmission of virus.

6 Claims, 12 Drawing Sheets

Specification includes a Sequence Listing.

(56) References Cited

OTHER PUBLICATIONS

Gordon, et al., "Prior dengue virus infection and risk of Zika: A pediatric cohort in Nicaragua", PLOS Pathogens, https://doi.org/10.1371/journal.pmed.1002726, Jan. 22, 2019, 16 pgs.
Pantoja, et al., "Zika virus pathogenesis in rhesus macaques is unaffected by pre-existing immunity to dengue virus", Nature Communication, www.nature.com/naturecommunications, Published Jun. 23, 2017, 13 pgs.
Shan, et al., "Maternal vaccination and protective immunity against Zika virus vertical transmission", Nature Communication, https://doi.org/10.1038/s41467-019-13589-1, 2019, 12 pgs.
Vidarsson, et al., "FcRn: an IgG receptor on phagocytes with a novel role in phagocytosis", Phagocytes, Blood, Nov. 15, 2006, vol. 108, No. 10, 7 pgs.
Vincent, et al., "Live Attenuated Influenza Vaccine Provides Superior Protection from Heterologous Infection in Pigs with Maternal Antibodies without Inducing Vaccine-Associated Enhanced Respiratory Disease", Journal of Virology, vol. 86, No. 19, Oct. 2012, 9 pgs.
Zheng, et al., "Microbiota-targeted maternal antibodies protect neonates from enteric infection", HHS Public Access, Nature, Jan. 2020, 577 (7791), 28 pgs.
Katzelnick, et al., "Zika virus infection enhances future risk of severe dengue disease," HHS Public Access, Science, Aug. 28, 2020; 369(6507): 1123-1128, 14 pages.

\* cited by examiner

Figure 4
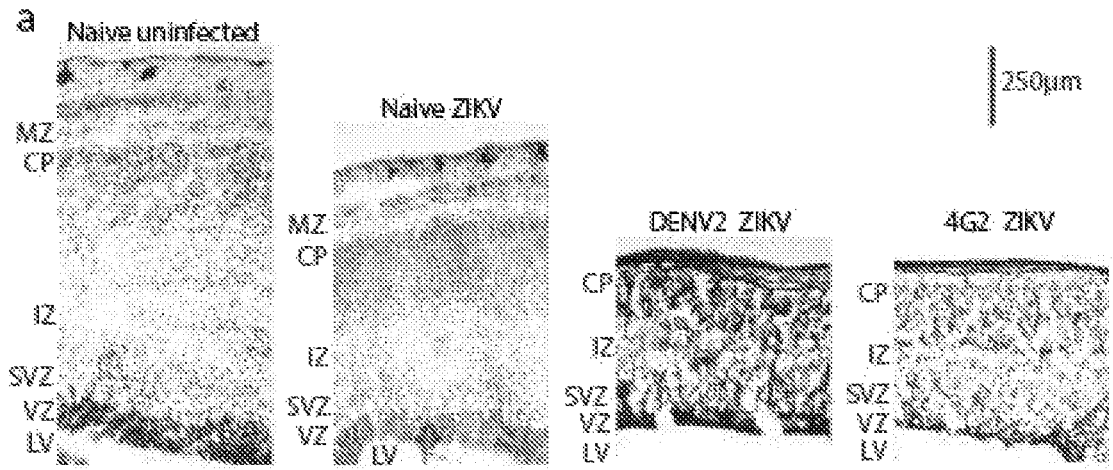
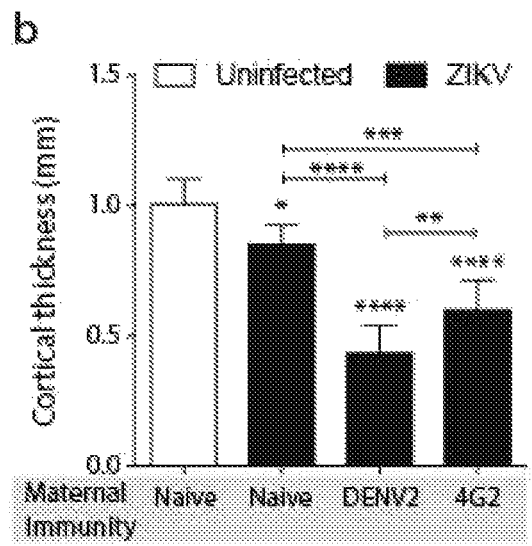
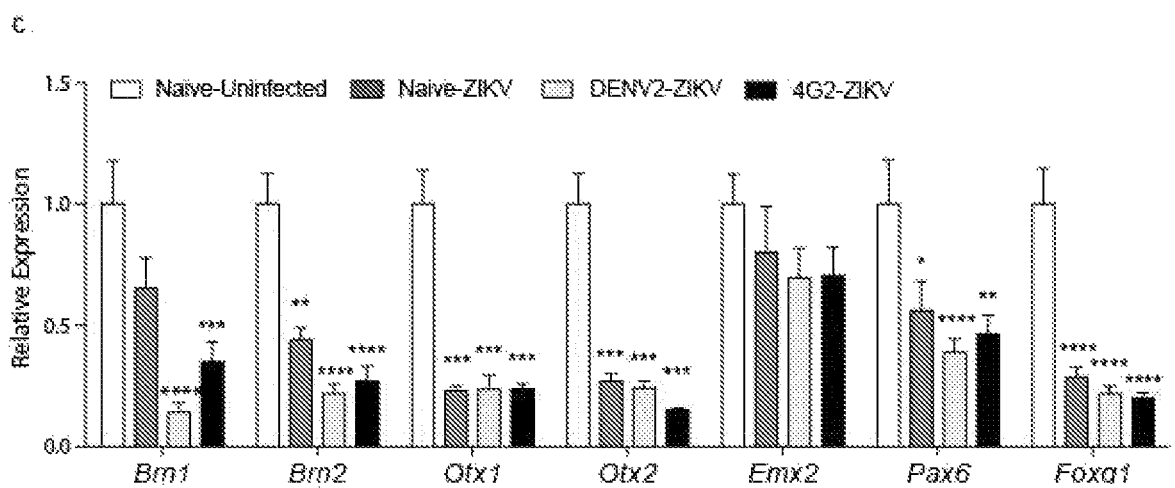

Figure 10

Human FcRN large subunit p51 precursor cDNA sequence

SEQ ID NO: 1: >ENA|BX647163|BX647163.1 Homo sapiens mRNA; cDNA DKFZp686H10220 (from clone DKFZp686H10220)

| | |
|---|---|
| ACAGGATGTGAGAGAGGAACTGGGGTCTCCAGTCACGGGAGCCAGGAGCCGGCCAGGGCC | 60 |
| GCAGGCAGGAAGGGAGCGAGGCTGAAGGGAACGTCGTCCTCTCAGCATGGGGGTCCCGCG | 120 |
| GCCTCAGCCCTGGGCGCTGGGGCTCCTGCTCTTTCTCCTTCCTGGGAGCCTGGGCGCAGA | 180 |
| AAGCCACCTCTCCCTCCTGTACCACCTTACCGCGGTGTCCTCGCCTGCCCCGGGGACTCC | 240 |
| TGCCTTCTGGGTGTCCGGCTGGCTGGGCCCGCAGCAGTACCTGAGCTACAATAGCCTGCG | 300 |
| GGGCGAGGCGGAGCCCTGTGGAGCTTGGGTCTGGGAAAACCAGGTGTCCTGGTATTGGGA | 360 |
| GAAAGAGACCACAGATCTGAGGATCAAGGAGAAGCTCTTTCTGGAAGCTTTCAAAGCTTT | 420 |
| GGGGGGAAAAGGTCCCTACACTCTGCAGGGCCTGCTGGGCTGTGAACTGGGCCCTGACAA | 480 |
| CACCTCGGTGCCCACCGCCAAGTTCGCCCTGAACGGCGAGGAGTTCATGAATTTCGACCT | 540 |
| CAAGCAGGGCACCTGGGGTGGGGACTGGCCCGAGGCCCTGGCTATCAGTCAGCGGTGGCA | 600 |
| GCAGCAGGACAAGGCGGCCAACAAGGAGCTCACCTTCCTGCTATTCTCCTGCCCGCACCG | 660 |
| CCTGCGGGAGCACCTGGAGAGGGGCCGCGGAAACCTGGAGTGGAAGGAGCCCCCCTCCAT | 720 |
| GCGCCTGAAGGCCCGACCCAGCAGCCCTGGCTTTTCCGTGCTTACCTGCAGCGCCTTCTC | 780 |
| CTTCTACCCTCCGGAGCTGCAACTTCGGTTCCTGCGGAATGGGCTGGCCGCTGGCACCGG | 840 |
| CCAGGGTGACTTCGGCCCCAACAGTGACGGATCCTTCCACGCCTCGTCGTCACTAACAGT | 900 |
| CAAAAGTGGCGATGAGCACCACTACTGCTGCATTGTGCAGCACGCGGGGCTGGCGCAGCC | 960 |
| CCTCAGGGTGGAGCTGGAATCTCCAGCCAAGTCCTCCGTGCTCGTGGTGGGAATCGTCAT | 1020 |
| CGGTGTCTTGCTACTCACGGCAGCGGCTGTAGGAGGAGCTCTGTTGTGGAGAAGGATGAG | 1080 |
| GAGTGGGCTGCCAGCCCCTTGGATCTCCCTTCGTGGAGACGACACCGGGGTCCTCCTGCC | 1140 |
| CACCCCAGGGGAGGCCCAGGATGCTGATTTGAAGGATGTAAATGTGATTCCAGCCACCGC | 1200 |
| CTGACCATCCGCCATTCCGACTGCTAAAAGCGAATGTAGTCAGGCCCCTTTCATGCTGTG | 1260 |
| AGACCTCCTGGAACACTGGCATCTCTGAGCCTCCAGAAGGGGTTCTGGGCCTAGTTGTCC | 1320 |
| TCCCTCTGGAGCCCCGTCCTGTGGTCTGCCTCAGTTTCCCCTCCTAATACATATGGCTGT | 1380 |
| TTTCCACCTCGATAATATAACACGAGTTTGGGCCCAAAAAAAAAAAAAAAAAAA | 1433 |

Figure 11

Human FcRN large subunit p51 precursor amino acid sequence

SEQ ID NO: 2

```
              10         20         30         40         50
MGVPRPQPWA LGLLLFLLPG SLGAESHLSL LYHLTAVSSP APGTPAFWVS
              60         70         80         90        100
GWLGPQQYLS YNSLRGEAEP CGAWVWENQV SWYWEKETTD LRIKEKLFLE
             110        120        130        140        150
AFKALGGKGP YTLQGLLGCE LGPDNTSVPT AKFALNGEEF MNFDLKQGTW
             160        170        180        190        200
GGDWPEALAI SQRWQQQDKA ANKELTFLLF SCPHRLREHL ERGRGNLEWK
             210        220        230        240        250
EPPSMRLKAR PSSPGFSVLT CSAFSFYPPE LQLRFLRNGL AAGTGQGDFG
             260        270        280        290        300
PNSDGSFHAS SSLTVKSGDE HHYCCIVQHA GLAQPLRVEL ESPAKSSVLV
             310        320        330        340        350
VGIVIGVLLL TAAAVGGALL WRRMRSGLPA PWISLRGDDT GVLLPTPGEA
             360
QDADLKDVNV IPATA
```

Figure 12
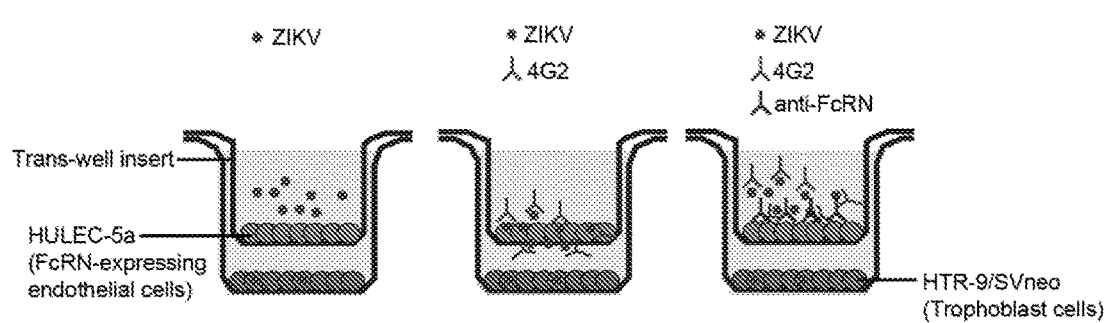
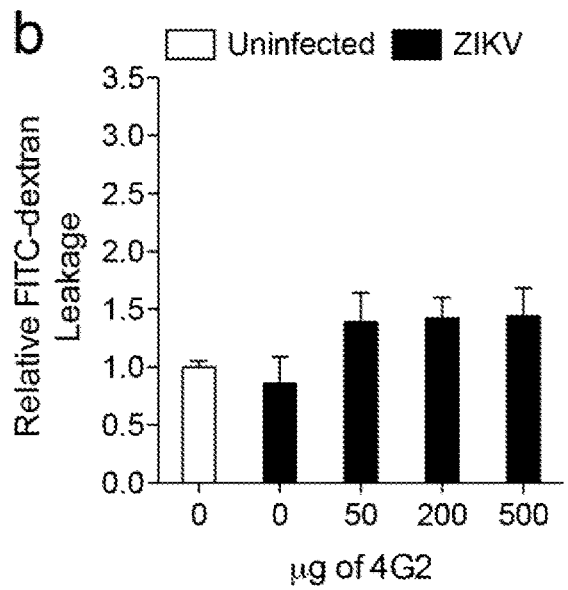
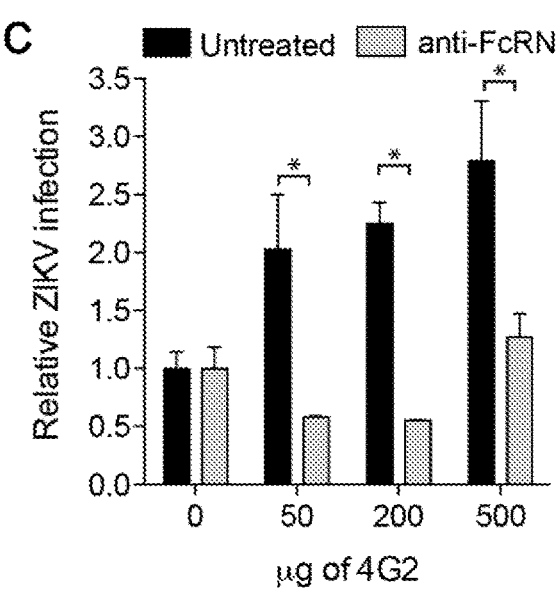

TARGETED PREVENTION OF MATERNAL TO FOETAL VERTICAL TRANSMISSION OF INFECTION

CROSS-REFERENCES TO RELATED APPLICATIONS

This application is a U.S. National Phase Application of PCT International Application No. PCT/SG2018/050228, filed on May 10, 2018, which is an International Application of and claims the benefit of priority to Singapore Patent Application No. 10201703861T, filed on May 11, 2017.

FIELD OF THE INVENTION

The present invention relates to targeted prevention of vertical transmission of infection between mother and foetus. More particularly the invention relates to methods of preventing FcRN-mediated transmission of virus, preferably ZIKV, from mother to foetus and to reagents that block or inhibit said FcRN-mediated transmission of virus.

BACKGROUND OF THE INVENTION

Zika virus (ZIKV) belongs to the family of Flaviviridae, which includes other arboviruses, such as dengue virus (DENV), Japanese encephalitis virus (JEV) and West Nile virus [Musso, D. & Gubler, D. J. Zika Virus. *Clin Microbiol Rev* 29: 487-524, (2016)]. ZIKV unexpectedly surfaced recently as a major public health concern due to the ongoing and spreading epidemic in South and Central America and the realization that it causes birth defects and neurological complications [Cauchemez, S. et al. *Lancet* 387: 2125-2132, (2016)]. Rarely, adults experience ZIKV-induced Guillain Barré syndrome, but microcephaly in infants is the most devastating and pressing symptom of ZIKV infection [Mlakar, J. et al. *N Engl J Med* 374: 951-958, (2016)]. It is suggested that the risk of microcephaly is higher when exposed to ZIKV during first trimester of pregnancy [Cauchemez, S. et al. *Lancet* 387: 2125-2132, (2016)]. Some studies have reported the direct effects of ZIKV infection on neuronal tissue damage [Wu, K. Y. et al. *Cell Res* 26: 645-654, (2016)]. However, not all ZIKV infections during pregnancy appear to result in brain abnormality during embryonic development and the mechanisms that lead to microcephaly in some foetuses but not others are yet to be understood.

Interestingly, ZIKV epidemic regions are often endemic for other flavivirus infections, particularly DENV. Due to the structural similarities between ZIKV and DENV, antibodies raised against one of the viruses are able to cross react with the others [Dejnirattisai, W. et al. *Nat Immunol*, 17(9): 1102-8 (2016)]. DENV antibodies can potentially promote antibody-dependent enhanced replication (ADE) of ZIKV in infected patients, which has been shown through ex vivo assays [Dejnirattisai, W. et al. *Nat Immunol*, 17(9): 1102-8 (2016)].

In view of the above lack of understanding of the mechanism of ZIKA virus infection-related birth defects during early stages of pregnancy, it is desirable to provide understanding of and methods to ameliorate or reduce the effects of ZIKV infection on unborn babies.

SUMMARY OF THE INVENTION

It has surprisingly been found that the Fc neonatal receptor (FcRN) receptor is involved in vertical transmission of ZIKV to a developing foetus.

Accordingly in a first aspect, the present invention provides an isolated reagent that blocks the maternal Fc neonatal receptor (FcRN) activity, reducing vertical transmission of virus infection from a mother to its developing foetus.

In a preferred embodiment of the invention, the isolated reagent inhibits trans-placental infection of the foetus by blocking maternal antibody-virus complex binding to the FcRN.

In a preferred embodiment of the invention, the mother has maternal antibodies that cross-react with a flavivirus.

According to another aspect, the present invention provides the use of an isolated reagent according to any aspect of the invention in the manufacture of a medicament for preventing vertical transmission of virus infection between mother and foetus by blocking maternal Fc neonatal receptor (FcRN) activity.

According to another aspect, the present invention provides a method of treatment to prevent vertical transmission of virus infection from mother to foetus, comprising administering to the mother an efficacious amount of an isolated reagent as herein defined.

BRIEF DESCRIPTION OF THE FIGURES

FIG. 4 shows that impaired cortical development in ZIKV-foetuses is enhanced by maternal DENV immunity. (a) Images of embryonic brain sections showing reduced cortical thickness in ZIKV-infected embryos. Tissue sections were cut to 15 μm thickness and nissl-stained using cresyl violet prior to imaging by light microscopy. Labels indicate the lateral ventricle (LV) and cortical regions: ventricular zone (VZ), sub-ventricular zone (SVZ), intermediate zone (IZ), cortical plate (CP) and marginal zone (MZ). (b) Quantification of cortical thickness from images. Error bars represent the SEM of average cortical thickness for individual foetuses obtained from 3 independent experiments; for naïve uninfected, n=5; naïve-ZIKV n=6; DENV2-ZIKV, n=7; 4G2-ZIKV, n=8. (c) Relative BRN-1 (transcription factor Brain 1, Brn1) expression in the mouse brains (normalized to Actin) as determined by real time RT-PCR. Relative expression of the following genes is also shown: Brain 2 (Brn2), orthodenticle homeobox genes 1 and 2 (OW, Otx2), empty spiracles homologue 2 (Emx2), Paired box 6 (Pax6), and fork-head box G1 (Foxg1). Error bars represent the SEM and n=5 foetuses per group. For b-c, * indicates $p<0.05$,  $p<0.01$, * $p<0.001$ and **** $p<0.0001$, as determined by 1-way ANOVA with Holm-Sidak's multiple comparison test. Variances do not differ amongst groups.

FIG. 10 shows the Human FcRN large subunit p51 precursor cDNA sequence.

FIG. 11 shows the Human FcRN large subunit p51 precursor amino acid sequence.

FIG. 12 shows that blockade of FcRN limits ZIKV transcytosis. (a) Schematic of the in vitro human culture system involving growing a monolayer of FcRN-expressing endothelial cells (HULEC-5A) on trans-well inserts, above infection-target cells, HTR-8/SVneo trophoblast cells. Combinations of ZIKV alone ($1.5\times10^5$ PFU per well, MOI of 0.1), ZIKV with various concentrations of the ZIKV cross-reactive antibody 4G2, or ZIKV+4G2 following pre-treatment with an antibody against FcRN (1 μg/ml) were applied to the top chambers. (b) Neither ZIKV nor ZIKV immune-complexed with 4G2 caused significant leakage of FITC-dextran across the monolayer at 24 h over levels in uninfected controls. FITC-dextran (1 mg/ml) was added to the top chamber at 24 h and measured in the bottom chamber after 1 h. (c) Trophoblast cells were harvested after 24 h from the bottom chamber and RNA was isolated to quantify ZIKV genome copies to measure infection burden. Application of antibody 4G2 with ZIKV to the top chamber enhanced infection of trophoblast target cells compared to ZIKV alone, in a concentration-dependent manner. Pre-treatment of endothelial monolayers with an anti-FcRN antibody (1 μg/ml) significantly blocked antibody-enhanced infection of trophoblast target cells. * indicates $p<0.01$.

DETAILED DESCRIPTION OF THE INVENTION

Figure 1:
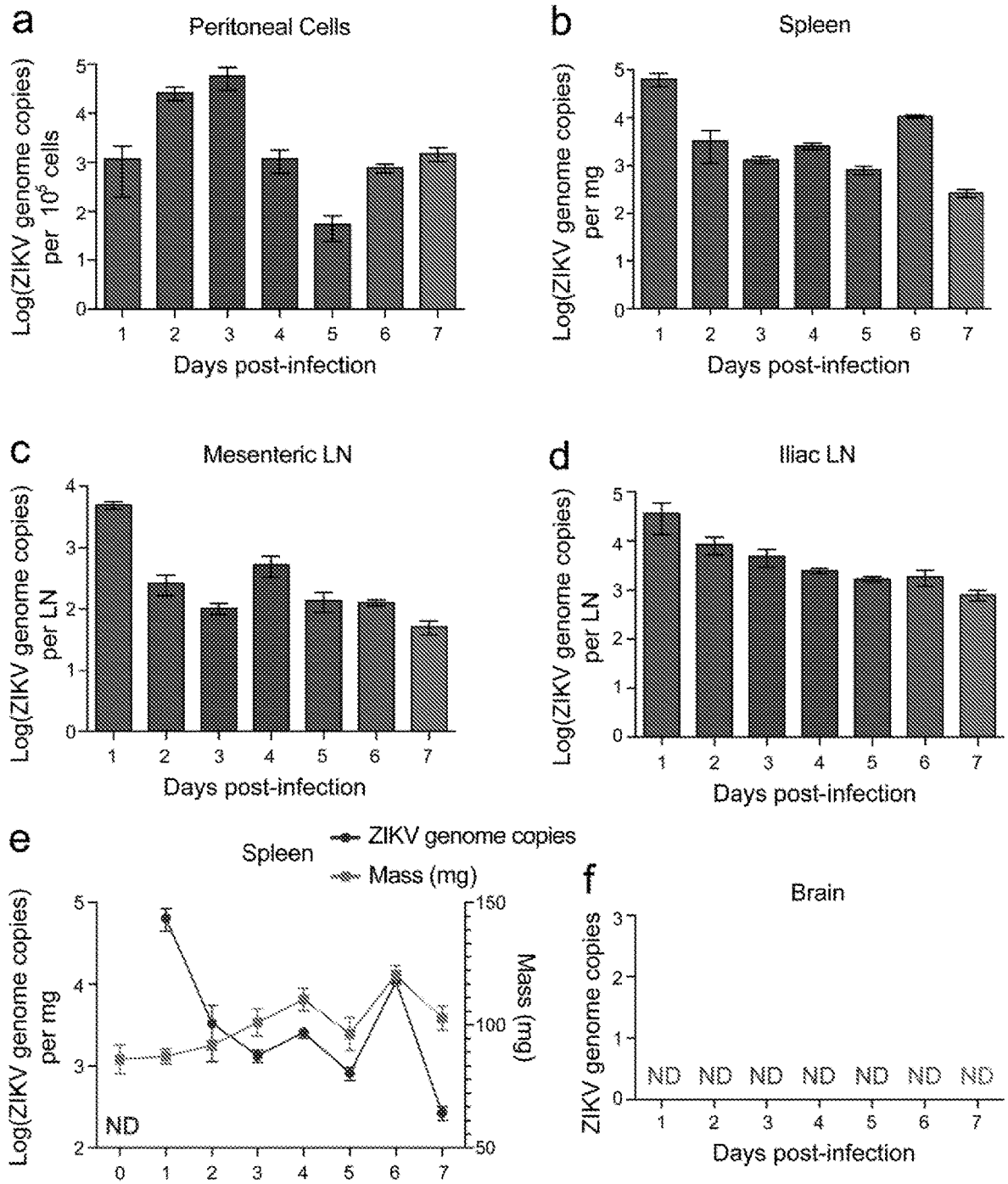
FIG. 1 shows sustained ZIKV infection in female immune-competent mice. ZIKV infection was quantified in peripheral tissues in (a) the cells isolated from the peritoneal cavity, (b) the spleen (c) the mesenteric lymph nodes (LN) and (d) iliac LNs, each day for 1 w following infection of female mice with $1 \times 10^6$ PFU of ZIKV, strain H/PF/2013. (e) ZIKV genome copies in the spleen are plotted with the splenic mass. (f) ZIKV was not detected (ND) in the brain of any animals. N=5 female mice per group. Error bars represent the SEM.

Bibliographic references mentioned in the present specification are for convenience listed in the form of a list of references and added at the end of the Examples. The whole content of such bibliographic references is herein incorporated by reference.

Definitions

For convenience, certain terms employed in the specification, examples and appended claims are collected here.

The term "antagonist," as it is used herein, refers to a molecule which, when bound to FcRN, blocks or decreases the amount or the duration of the effect of the biological activity of FcRN. In a preferred aspect, the antagonist blocks or decreases transcytosis of antibody-virus complexes across the placenta from mother to foetus. Antagonists may include proteins, nucleic acids, carbohydrates, antibodies, or any other molecules which decrease the effect of FcRN.

As used herein, the term "antibody" refers to any immunoglobulin or intact molecule as well as to fragments thereof that bind to a specific epitope. More particularly, the term "antibody" refers to anti-FcRN antibodies [Christianson, G. J. et al. *MAbs* 4: 208-216, (2012)], "affibodies" or other modified antibodies that have FcRN binding/blocking activity similar to antibodies [Seijsing, J. et al. *Proc Natl Acad Sci USA* 111: 17110-17115, (2014)]. Such antibodies may target FcRN or the Fc portion of the maternal antibody-ZIKV complex and include, but are not limited to, polyclonal, monoclonal, chimeric, humanised, single chain, single chain fragment variable (scFv), Fab, Fab', F(ab)' fragments and/or F(v) portions of the whole antibody. The term "monoclonal antibody" may be referred to as "Mab". The antibodies include antibody 4C9, produced by the hybridoma cell line having ATCC deposit number CRL-2437.

The term "antibody fragment" as used herein refers to an incomplete or isolated portion of the full sequence of the antibody which retains the antigen binding function of the parent antibody. Examples of antibody fragments include scFv, Fab, Fab', F(ab')2, and Fv fragments; diabodies; linear antibodies; single-chain antibody molecules; and multi-specific antibodies formed from antibody fragments. Fragments of the 4C9 antibodies are encompassed by the invention so long as they retain the desired affinity of the full-length antibody. In particular, it may be shorter by at least one amino acid.

The term "antigen" as used herein, refers to a substance that prompts the generation of antibodies and can cause an immune response. It may be used interchangeably in the present invention with the term "immunogen". In the strict sense, immunogens are those substances that elicit a response from the immune system, whereas antigens are defined as substances that bind to specific antibodies. An antigen or fragment thereof may be a molecule (i.e. an epitope) that makes contact with a particular antibody. When a protein or a fragment of a protein is used to immunize a host animal, numerous regions of the protein may induce the production of antibodies (i.e. elicit the immune response), which bind specifically to the antigen (given regions or three-dimensional structures on the protein). A non-limiting example of an antigen is the FcRN polypeptide, the human FcRN nucleotide and amino acid sequences of which are shown in FIGS. 10 (SEQ ID NO: 1) and 11 (SEQ ID NO: 2). More specifically, an antigen may comprise the human FcRN peptide sequence comprising GEEFMNFDLKQGT (SEQ ID NO: 3). In particular, the term "epitope" may refer to a consecutive sequence of from about 5 to about 13 amino acids which form an antibody binding site. The epitope in the form that binds to the antibodies or binding protein may be a denatured protein that is substantially devoid of tertiary structure. The epitope may be a conformational epitope that comprises non-consecutive elements from non-consecutive sequences. The epitope may also be a quaternary epitope which comprises non-consecutive elements from more than one protein or polypeptide which are assembled into an FcRN.

As used herein, the term "aptamers" is to be interpreted as specifying oligonucleotide or peptide molecules that bind to a specific target molecule. Aptamers are usually created by selecting them from a large random sequence pool, but natural aptamers also exist in riboswitches.

As used herein, the term "comprising" or "including" is to be interpreted as specifying the presence of the stated features, integers, steps or components as referred to, but does not preclude the presence or addition of one or more features, integers, steps or components, or groups thereof. However, in context with the present disclosure, the term "comprising" or "including" also includes "consisting of". The variations of the word "comprising", such as "comprise" and "comprises", and "including", such as "include" and "includes", have correspondingly varied meanings.

The term "chimeric antibody," as used herein, refers to at least one antibody molecule in which the amino acid sequence in the constant regions has been altered so that the antibody more closely resembles a human antibody, and still retains its original binding ability. For example, a chimeric antibody is a molecule in which different portions are derived from different animal species, such as those having a variable region derived from a murine antibody and a human immunoglobulin constant region. Chimeric antibodies include those that contain a human Fc portion and a murine (or other non-human) Fv portion.

The term "humanized antibody", as used herein, refers to at least one antibody molecule in which the amino acid sequence within the variable and constant regions has been altered so that the antibody more closely resembles a human antibody, and still retains its original binding ability. For example, humanized antibodies include antibody molecules from non-human species having one or more CDRs from the non-human species and a framework region from a human immunoglobulin molecule.

As used herein, the term "hybridoma" refers to cells that have been engineered to produce a desired antibody in large amounts. For example, to produce at least one hybridoma, B cells are removed from the spleen of an animal that has been challenged with the relevant antigen and fused with at least one immortalized cell. This fusion is performed by making the cell membranes more permeable. The fused hybrid cells (called hybridomas), will multiply rapidly and indefinitely and will produce at least one antibody. An example of a hybridoma is the antibody 4C9 hybridoma cell line having ATCC deposit number CRL-2437.

The term "immunological binding characteristics" of an antibody or related binding protein, in all of its grammatical forms, refers to the specificity, affinity and cross-reactivity of the antibody or binding protein for its antigen.

The term "isolated" is herein defined as a biological component (such as a nucleic acid, peptide or protein) that has been substantially separated, produced apart from, or purified away from other biological components in the cell of the organism in which the component naturally occurs, i.e., other chromosomal and extra-chromosomal DNA and RNA, and proteins. Nucleic acids, peptides and proteins which have been isolated thus include nucleic acids and proteins purified by standard purification methods. The term also embraces nucleic acids, peptides and proteins prepared by recombinant expression in a host cell as well as chemically synthesized nucleic acids.

The term "sample," as used herein, is used in its broadest sense. A biological sample suspected of containing nucleic acids encoding at least one ZIKV derived peptide, or fragments thereof, ZIKV itself and/or maternal DENV antibodies may comprise a bodily fluid, an extract from a cell, chromosome, organelle, or membrane isolated from a cell, a cell, genomic DNA, RNA, or cDNA (in solution or bound to a solid support), a tissue, a tissue print and the like.

The term "small molecules" is herein defined as low molecular weight molecules that include lipids, monosaccharides, second messengers, other natural products and metabolites, as well as drugs and other xenobiotics. A small molecule may have a low molecular weight (<900 daltons) and be an organic compound.

As used herein, the terms "specific binding" or "specifically binding" refer to the interaction between one or more proteins or peptides and an agonist, an antibody, or an antagonist. In particular, the binding is between an antigen and an antibody and/or between FcRN and the Fc region of a maternal antibody, or between FcRN and a blocking reagent. The interaction is dependent upon the presence of a particular structure of the one or more proteins recognized by the binding molecule (i.e., the antigen or epitope). As described hereinbefore, the antigen or epitope may be comprised of more than a single peptide sequence from the same protein or different proteins which come together spatially to form a conformational antigen or epitope. For example, if an antibody is specific for epitope "A", the presence of a polypeptide containing the epitope A, or the presence of free unlabelled A, in a reaction containing free labelled A and the antibody will reduce the amount of labelled A that binds to the antibody.

The term "subject" is herein defined as vertebrate, particularly mammal, more particularly human. For purposes of research, the subject may particularly be at least one animal model, e.g., a mouse, rat and the like. In particular, for treatment of flavivirus infection and/or flavivirus-linked diseases, preferably ZIKV infection and/or ZIKV-linked diseases, the subject may be a human infected by a flavivirus, preferably ZIKV and may also be DENV-immune. More particularly the subject is a pregnant female.

The term "treatment", as used in the context of the invention refers to prophylactic, ameliorating, therapeutic or curative treatment.

The term "variant" as used herein, refers to an amino acid sequence that is altered by one or more amino acids, but retains the ability to recognize and bind the same epitope on FcRN as the non-variant reference sequence. The variant may have "conservative" changes, wherein a substituted amino acid has similar structural or chemical properties (e.g., replacement of leucine with isoleucine). More rarely, a variant may have "non-conservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR® software (DNASTAR, Inc. Madison, Wis., USA). For example, a humanized 4C9 variable light chain amino acid sequence may be created by substituting amino acids in the 4C9 variable light chain amino acid sequence with preferred human framework and may be considered a variant of 4C9 variable light chain.

The inventors have found that flaviviruses such as ZIKV can be transmitted from an infected mother to her unborn foetus by a mechanism where circulating antibodies that bind to ZIKV form a complex whereby the antibody Fc portion of the antibody then binds to FcRN at the placenta and is transcytosed to the foetus. Moreover, the inventors have found that Dengue-immune antibodies that cross-react with ZIKV can facilitate transcytosis of ZIKV to the foetus via FcRN binding of antibody-ZIKV complex, which may explain why microcephaly is more prevalent in babies born in regions which also have DENV.

According to a first aspect, the present invention provides an isolated reagent that blocks the maternal Fc neonatal receptor (FcRN) activity, reducing vertical transmission of virus infection from a mother to its developing foetus.

In another preferred embodiment of the invention, the isolated reagent inhibits trans-placental infection of the foetus by blocking maternal antibody-virus complex binding to the FcRN.

In another preferred embodiment of the invention, the isolated reagent is selected from the group comprising proteins, nucleic acids, aptamers, carbohydrates, antibodies or fragments thereof and any other molecules that can block FcRN activity.

Various strategies have been used experimentally to prevent transport of IgG by FcRN receptors. Most are biologics that either block the FcRN receptor by binding to it [Christianson, G. J. et al. *MAbs* 4: 208-216, (2012)], bind to the Fc portion of IgG to prevent binding to FcRN [Sockolosky, J. T., et al. *PLoS One* 9: e102566, (2014)], or are modified antibodies [Seijsing, J. et al. *Proc Natl Acad Sci USA* 111: 17110-17115, (2014)] or peptides [Sockolosky, J. T., et al. *PLoS One* 9: e102566, (2014); Mezo, A. R. et al. *Proc Natl Acad Sci USA* 105: 2337-2342, (2008)] that target these two sites.

Examples of available strategies include:

Anti-FcRN antibodies [Christianson, G. J. et al. *MAbs* 4: 208-216, (2012)];

"Affibodies" or other modified antibodies that have FcRN binding/blocking activity similar to antibodies [Seijsing, J. et al. *Proc Natl Acad Sci USA* 111: 17110-17115, (2014)];

Single-chain Fc (scFc) polypeptides [Qiu, Y., et al. *J Control Release* 229: 37-47, (2016); Kenanova, V. et al. *Cancer Res* 65: 622-631 (2005)];

6-amino acid peptide dimer SYN14363 [Mezo, A. R. et al. *Proc Natl Acad Sci USA* 105: 2337-2342, (2008)];

FcRN binding polypeptides and their characteristics described in WO 00/42072;

Intravenous immunoglobulin (IVIg) which saturates the binding of FcRN with other antibodies [Berger, M., et al. *J Peripher New Syst* 18: 275-296, (2013)];

IgG or IgY which are specific monoclonal antibodies that work similarly to IVIg [Sesarman, A., et al. *Cell Mol Life Sci* 67: 2533-2550, (2010)];

Fragment B of Staphylococcal protein A [Raghavan, M., et al. *Immunity* 1: 303-315 (1994)];

IgG antagonists (e.g. FcIII also known as gG-Fc binding peptide (IgGBP) when attached to another protein [Sockolosky, J. T., et al. *PLoS One* 9: e102566, (2014)]); and Small molecules, such as various 2,3-dichloroquinoxaline analogs [Wang, Z., et al. *Bioorg Med Chem Lett* 23: 1253-1256, (2013)].

It would be understood by a person skilled in the art that a preferred aspect of the present invention is to block vertical transmission of virus via FcRN and that the invention includes but is not limited to use of any one or more of the above strategies. It may also be possible to use an antibody against a virus, such as a flavivirus, more preferably DENV or ZIKV, which has a mutated Fc region and/or hinge region to prevent binding to FcRN and other Fc receptors.

Competitive binding antibodies have blocking and neutralizing activity based on binding to the sites involved in antibody binding to FcRN. These antibodies are generally thought to be the CH2 and CH3 domains of IgG and the α1 and α2 domains of FcR [Raghavan, M., et al. *Immunity* 1: 303-315 (1994)]. Non-competitive binding antibodies bind to a different site. In theory, since interaction with non-competitive binding antibodies does not involve the actual binding site, the antibodies would be assumed to be functioning as allosteric inhibitors [Roopenian, D. C. & Akilesh, S. *Nat Rev Immunol* 7: 715-725, (2007)]. WO/2007/087289, incorporated herein by reference, describes some non-competitive antibodies.

There are sites on both the heavy and light chain of FcRN that can influence the binding of IgG to FcRN and there are antibodies that target both regions. Antibodies targeting the heavy chain of FcRN have been described in WO/2007/087289. Antibody 4C9 disclosed in WO/2007/087289 targets the light chain of rat FcRN but is considered to bind the heavy chain of human FcRN.

In another preferred embodiment of the invention, the agent is an antibody or fragment thereof. The antibody or fragment thereof may be a competitive or non-competitive inhibitor of binding of the maternal antibody-virus complex to the FcRN.

In another preferred embodiment of the invention, the antibody is selected from the group comprising monoclonal mouse, human, humanized or chimeric antibody or fragment thereof.

The antibodies of the present invention may be produced by any technique that provides for the production of antibody molecules by continuous cell lines in culture. Such methods include, but are not limited to, the hybridoma technique originally developed in 1975 by Kohler and Milstein [*J Immunol* 174: 2453-2455 (2005)], as well as the trioma technique, the human B-cell hybridoma technique and the EBV-hybridoma technique to produce human monoclonal antibodies [Cole et al., *Monoclonal Antibodies and Cancer Therapy* Alan R. Liss, Inc., pp 77-96 (1985)]. Human antibodies can be used and can be obtained by using human hybridomas [Cote et al., *Proc Natl Acad Sci USA* 80: 2026-2030 (1983)]. Additionally, once antibody sequences are known production can be achieved using standard recombinant technologies well known in the art.

Techniques developed for the production of chimeric antibodies [Morrison, et al., *Proc Natl Acad Sci USA* 81: 6851-6855 (1984)] incorporated herein by reference in its entirety), by splicing the genes from a mouse antibody molecule of appropriate antigen specificity together with genes from a human antibody molecule of appropriate biological activity, can be used. For example, the genes from a mouse antibody molecule such as 4C9 can be spliced together with genes from a human antibody molecule of appropriate biological activity.

Techniques have been developed for the production of humanized antibodies (e.g., U.S. Pat. Nos. 5,585,089 and/or 5,225,539, which are incorporated herein by reference in their entirety). An immunoglobulin light or heavy chain variable region consists of a "framework" region interrupted by three hypervariable regions, referred to as complementarity determining regions (CDRs). Both chimeric and humanized antibodies may be monoclonal. Such human or humanized chimeric antibodies may be preferred for use in in vivo diagnosis or therapy of human diseases or disorders.

In the production of antibodies, screening for the desired antibody can be accomplished by techniques known in the art. For example, these techniques may include but are not limited to radioimmunoassay, enzyme-linked immunosorbent assay (ELISA), "sandwich" immunoassays, immunoradiometric assays, gel diffusion precipitin reactions, immunodiffusion assays, in situ immunoassays (using colloidal gold, enzyme, radioisotope labels or the like), western blots, precipitation reactions, agglutination assays (gel agglutination assays, haemagglutination assays or the like), immunofluorescence assays, immunoelectrophoresis assays and the like. For example, the antibody binding may be detected by detecting a label on the primary antibody. In another example, the primary antibody may be detected by detecting binding of a secondary antibody or other reagent to the primary antibody. The secondary antibody may be labelled.

Based on the findings herein, it is quite possible that other viruses which pass from mother to foetus, such as HIV, rubella, cytomegalovirus, herpes simplex viruses, chickenpox, coxsackievirus, HTLV, Hepatitis B and Parvo virus, can be vertically transmitted to a foetus via antibody-virus complex binding to the FcRN. More particularly, it is likely that other flaviviruses can be vertically transmitted to a foetus via antibody-virus complex binding to the FcRN.

In a preferred embodiment, the isolated reagent blocks or inhibits FcRN-mediated transmission of a flavivirus, wherein the flavivirus is selected from the group comprising DENV, ZIKV, Yellow fever (YFV), Japanese encephalitis, West Nile virus (WNV) and Hepatitis C virus (HCV).

In another preferred embodiment, the isolated reagent according to any aspect of the invention blocks vertical transmission of Zika virus.

In the Examples it is shown that pregnant females that carry cross-reactive antibodies, either due to immunity (for example from a prior DENV infection) or artificially administered (for example that are DENV-directed but ZIKV cross-reactive), are capable of forming antibody-virus complexes which are transmitted via the FcRN to the unborn foetus.

In another preferred embodiment, the mother is immune to a cross-reactive virus. In another preferred embodiment, the mother is flavivirus-immune.

In another preferred embodiment, the mother is Dengue virus-immune.

In another preferred embodiment, the antibody is directed to an epitope in human FcRN comprising the amino acid SEQ ID NO: 2.

In another preferred embodiment, the antibody or fragment thereof binds with specificity to the heavy chain of human FcRN, preferably an FcRN peptide sequence comprising GEEFMNFDLKQGT (SEQ ID NO: 3). Preferably, the antibody is 4C9 (hybridoma ATCC #CRL-2437) or a humanized or chimeric antibody form or fragment thereof.

In another preferred embodiment, the isolated reagent according to any aspect of the invention is selected from the group comprising single-chain Fc (scFc) polypeptides [Qiu, Y., et al. *J Control Release* 229: 37-47, (2016); Kenanova, V. et al. *Cancer Res* 65: 622-631 (2005)]; 6-amino acid peptide dimer SYN1436 [Mezo, A. R. et al. *Proc Natl Acad Sci USA* 105: 2337-2342, (2008)]; FcRN binding polypeptides (such as those described in WO 00/42072); IVIG [Berger, M., et al. *J Peripher New Syst* 18: 275-296, (2013)]; IgG or IgY [Sesarman, A., et al. *Cell Mol Life Sci* 67: 2533-2550, (2010)]; fragment B of Staphylococcal protein A [Raghavan, M., et al. *Immunity* 1: 303-315 (1994)]; IgG antagonists (e.g. FcIII also known as IgG-Fc binding peptide (IgGBP) when attached to another protein [Sockolosky, J. T., et al. *PLoS One* 9: e102566, (2014)]); aptamers and small molecules such as various 2,3-dichloroquinoxaline analogs [Wang, Z., et al. *Bioorg Med Chem Lett* 23: 1253-1256, (2013)].

According to another preferred aspect of the invention, there is provided the use of an isolated reagent according to any aspect of the invention in the manufacture of a medicament for preventing vertical transmission of virus infection between mother and foetus by blocking maternal Fc neonatal receptor (FcRN) activity.

In a preferred embodiment, the virus infection is caused by a virus which passes from mother to foetus, such as from the group comprising HIV, rubella, cytomegalovirus, herpes simplex viruses, chickenpox, coxsackievirus, HTLV, Hepatitis B and Parvo virus. More preferably, the virus infection is caused by a flavivirus.

In another preferred embodiment, the virus infection is caused by a flavivirus selected from the group comprising DENV, ZIKV, Yellow fever (YFV), Japanese encephalitis, West Nile virus (WNV) and Hepatitis C virus (HCV).

In another preferred embodiment, the virus infection is caused by Zika virus.

In another preferred embodiment, the medicament is for preventing vertical transmission of a virus to a mother who is immune to a cross-reactive virus.

In another preferred embodiment, the mother is flavivirus-immune. More preferably, the mother is DENV-immune.

In another preferred embodiment, the medicament is for preventing vertical transmission of flavivirus to a mother who is in the first trimester of pregnancy.

In a preferred embodiment, the medicament is for preventing vertical transmission of Zika virus.

In another preferred embodiment, the medicament reduces the incidence of microcephaly in the foetus.

According to another preferred aspect of the invention, there is provided a method of treatment to prevent vertical transmission of a virus infection from mother to foetus, comprising administering to the mother an efficacious amount of an isolated reagent as defined according to any aspect of the invention.

In a preferred embodiment, the virus infection is caused by a virus which passes from mother to foetus, such as from the group comprising HIV, rubella, cytomegalovirus, herpes simplex viruses, chickenpox, coxsackievirus, HTLV, Hepatitis B and Parvo virus.

More preferably, the virus infection is caused by a flavivirus.

In another preferred embodiment, the virus infection is caused by a flavivirus selected from the group comprising DENV, ZIKV, Yellow fever (YFV), Japanese encephalitis, West Nile virus (WNV) and Hepatitis C virus (HCV).

In a preferred embodiment, the virus infection is caused by Zika virus.

In another preferred embodiment, the method comprises blocking maternal antibody-virus complex binding to the FcRN with an antibody selected from the group comprising monoclonal mouse, human, humanized or chimeric antibody or fragment thereof.

In another preferred embodiment, the antibody is directed to an epitope in human FcRN comprising the amino acid SEQ ID NO: 2.

In another preferred embodiment, the antibody or fragment thereof binds with specificity to the heavy chain of human FcRN, preferably an FcRN peptide sequence comprising GEEFMNFDLKQGT. Preferably, the antibody is 4C9 (hybridoma ATCC #CRL-2437) or a humanized or chimeric antibody form or fragment thereof.

In another preferred embodiment, the method treats a mother who is immune to a cross-reactive virus.

In another preferred embodiment, the mother is flavivirus-immune.

In another preferred embodiment, the method is for preventing vertical transmission of virus to a mother who is in the first trimester of pregnancy.

In another preferred embodiment, the method treats a mother who is Dengue virus-immune. If the mother is DENV-immune she will likely have maternal antibodies that also bind other flaviviruses such as Zika virus. It is demonstrated herein that if the mother is DENV-immune, subsequent Zika virus infection results in a higher incidence of foetal infection and microcephaly than if the mother is not carrying cross-reactive maternal antibodies. Treatment with FcRN-blocking agents reduced the incidence of microcephaly in DENV-immune animals subsequently infected by Zika virus.

In another preferred embodiment, the method treats a mother that is flavivirus-immune and infected with Zika virus.

In another preferred embodiment, the treatment reduces the incidence of microcephaly in the foetus compared to if the mother is untreated.

In another preferred embodiment of any aspect of the invention, the mother and foetus are human.

A person skilled in the art will appreciate that the present invention may be practised without undue experimentation according to the method given herein. The methods, techniques and chemicals are as described in the references given or from protocols in standard biotechnology and molecular biology text books.

Having now generally described the invention, the same will be more readily understood through reference to the following Examples which are provided by way of illustration, and are not intended to be limiting of the present invention.

EXAMPLES

Standard molecular biology techniques known in the art and not specifically described were generally followed as described in Green and Sambrook, Molecular Cloning: A Laboratory Manual, Cold Springs Harbor Laboratory, New York (2012).

Example 1

Materials and Methods

Virus Production

ZIKV strain H/PF/2013 (European Virus Archive) [Baronti, C. et al. *Genome Announc* 2: e00500-14 (2014)] and DENV2 strain Eden2 were produced in C6/36 mosquito cells (ATCC) in RPMI-1640 with 2% foetal bovine serum (FBS) and 1% penicillin and streptomycin at 28° C. and harvested after 5 d. Viral titers were quantified by a standard plaque assay using BHK21 (ATCC) cell monolayers. Cell lines have been validated to be mycoplasma free.

Mouse Infections

Female C57Bl/6NTac mice and $FcRN^{-/-}$ mice (6-8 w old, Jackson Laboratory) were used for experiments. To determine the time course of ZIKV infection in female mice, groups of 5 mice were given $1\times10^6$ PFU, of ZIKV by i.p. injection in a 100 μL volume of saline. Tissues were harvested upon necropsy at the indicated time points for further analysis. To generate DENV2-immune mothers, female mice were injected with DENV2 ($1 \times 10^6$ PFU, i.p.), 21 days prior pairing with a male. ELISAs were performed using serum isolated day 21 post DENV2 infection against DENV and ZIKV antigens that were purified by ultracentrifugation on a sucrose cushion to ensure ELISA plates were coated with only virus structural antigens. Endpoint titers were considered positive at 2-fold over naïve. Alternatively, naïve mice, or mice that had been given the 4G2 antibody (ATCC, HB-112) by i.p, injection (50 μg/mouse) 24 h previously were paired with male mice for breeding. The female mice were monitored daily for successful mating, after which the male mice were removed. Mice were injected on E7 with ZIKV at $1 \times 10^6$ PFU by i.p. injection, or with an equivalent volume of saline as a control. At E10 or E18, the mother mice were sacrificed and the foetuses and mothers' spleens were collected. Incidence of microcephaly was determined based on head circumference below the $3^{rd}$ percentile of healthy uninfected control foetuses. The Institutional Animal Care and Use Committee approved all animal protocols.

Quantification of ZIKV Infection in Adult and Foetal Mice.

For adult mice, the spleen, liver, brain, peritoneal lavage, mesenteric and iliac lymph nodes (LNs) were collected at the indicated time points. For E10 foetuses, the foetuses were extracted from the yolk sac and the amniotic cavity under a stereo microscope (Olympus SZ61). Whole foetuses and placentas were collected for RNA extraction and the mother's spleen was collected concurrently. The RNA from the liver, the spleen, the brain, and E10 foetuses was extracted using the TRIzol reagent (Invitrogen). For the mesenteric LNs, the iliac LNs, the cells from the peritoneal lavage and placentas, the RNA was extracted using RNAeasy mini kit (Qiagen). The Superscript III Platinum One-step qRT-PCR kit (Invitrogen) was used according to the manufacturer's instructions to produce cDNA. Validated ZIKV-specific primers [Lanciotti, R. S. et al. *Emerg Infect Dis* 14: 1232-1239, (2008)] (forward: 5'-CCGCTGCC-CAACACAAG, SEQ ID NO: 4; reverse: 5'-CCACTAACGTTCTTTTGCAGACAT, SEQ ID NO: 5); and a FAM-probe (AGCCTACCTTGACAAGCAGTCA-GACACTCAA; SEQ ID NO: 6) were used. A plasmid containing the ZIKV region of interest was used to generate a standard curve to quantify genome copies. RNA from each uninfected mouse tissue was used as a negative control for all assays.

Expression of Transcription Factors

To quantitate expression of transcription factors associated with neurological development in foetal brains, RNA was extracted, as above, using the TRIzol reagent. The iScript cDNA synthesis kit (Biorad) was used according to the manufacturer's instructions to generate cDNA. Real-time PCR was performed using SYBR green reagent (Biorad). Expression of the housekeeping gene actin was used to calculate the ΔΔCq value and gene expression was measured using the following specific mouse primers:

```
Bm1 forward:
                                         SEQ ID NO: 7;
5'-CTCGGCGCAGGAAATCAC, reverse:
                                         SEQ ID NO: 8;
5'-CCCGCACGACCTCCTTT, Bm2 forward:
                                         SEQ ID NO: 9;
5'- CCATTTCCTCAAATGCCCTA, reverse:
                                         SEQ ID NO: 10;
5'-GGAGGGGTCATCCTTTTCTC, Otx1 forward:
                                         SEQ ID NO: 11;
5'-AAGACAAGCCACTCCGACAA, reverse:
                                         SEQ ID NO: 12;
5'-GCGAAGTCCTTCAAGCTGTT, Otx2 forward:
                                         SEQ ID NO: 13;
5'-GGAAGAGGTGGCACTGAAAA, reverse:
                                         SEQ ID NO: 14;
5'-CTGACCTCCATTCTGCTGCT, Emx2 forward:
                                         SEQ ID NO: 15;
5'-ACCTTCTACCCCTGGCTCAT, reverse:
                                         SEQ ID NO: 16;
5'-GAATCCGCTTTGGCTTTCT, Pax6 forward:
                                         SEQ ID NO: 17;
5'-CTAAGGATGTTGAACGGGCA, reverse:
                                         SEQ ID NO: 18;
5'-AGTTGGTGTTCTCTCCCCCT, Foxg1 forward:
                                         SEQ ID NO: 19;
5'-TGGAAGGCCTCCACAGAAC, reverse
                                         SEQ ID NO: 20;
5'-TGGCAAGGCATGTAGCAA,
and actin control:
forward:
                                         SEQ ID NO: 21;
5'-CGTCGACAACGGCTCCGGC, reverse:
                                         SEQ ID NO: 22.
5'-GGTGTTGAAGGTCTCAAACATGATCTGGG,
``` cDNA from uninfected embryos was used as a negative control.

Tissue Preparation and Histology

Upon recovery of the foetuses, they were fixed in 4% paraformaldehyde overnight at 4° C. and cryopreserved by soaking in a 30% sucrose solution at 4° C. for 24-48 h, until the foetus was no longer floating and completely immersed in the solution. The foetuses were then transferred to a 1:1 mixture of OCT (Sakura):30% sucrose and rocked for 30 min at room temperature. The foetuses were then transferred to molds with OCT and snap-frozen on dry ice before storage at −80° C. Cryo-sections (15 μm thickness) were made using a Leica cryostat. For Nissl staining, air dried sections were rinsed in distilled water for 5 min before dehydration using graded series of ethanol (50%, 70%, 95%, 100%) for 5 min each followed by 3 changes in xylene. Dehydrated slides were then rehydrated using a graded series of ethanol (100%, 95%, 70%, 50% and 30%) for 5 min each before being washed in distilled water for 5 min. Slides were stained with 0.1% of cresyl violet stain for 5-10 min, followed by washing twice in distilled water for 5 min each. Stained slides were then dehydrated using graded series of ethanol and cleared in xylene 2-3 times (5 min each) before being mounted with permount using a glass coverslip. For immunohistochemistry, formalin fixed sections were permeabilized using 100% acetone at −20° C. for 30 min followed by additional step of permeabilization using 1% Triton x-100 in Tris buffer saline (TBS) for 1 h at room temperature. Next, tissue sections were blocked using 10% FBS+2% BSA in TBS for 2 h, before incubation with primary antibodies. ZIKV-specific antibodies against M (GTX133305, GeneTex) and NS2B (GTX133308, GeneTex) proteins or antibodies against Pax6 (ab5790, Abcam) or Brn1 (NBP1-49872, Novus Biologicals) were incubated at 1:100-200 dilutions overnight at 4° C. Sections were washed with TBS 4-times for 30 min each. Endogenous peroxidase activity was reduced by 0.3% $H_2O_2$ in TBS treatment for 30 min at room temperature. Sections were washed once with TBS and incubated with secondary HRP-conjugated antibodies against rabbit or goat IgG (Jackson Immuno Research) at a dilution of 1:1000 for 1 h at room temperature. Following secondary antibody treatment, sections were extensively washed (4-5 times for 30 min each time using TBS) and developed using 3,3'-Diaminobenzidine (DAB) Enhanced Liquid Substrate System tetrahydrochloride for Immunohistology (D3939, Sigma). Substrate development was allowed for maximum of 10 min followed by washing twice with distilled water. Finally, sections were dehydrated in graded series of ethanol, cleared with xylene, and mounted, as above. Images were obtained using a light microscope (Nikon) and cortical thickness was measured using ImageJ software.

Statistical Analysis

Statistics were performed using Prism and Excel software packages. Groups were not blinded and no randomization procedures were performed for this study. Sample sizes were not estimated in advance of the studies. Animals were not excluded from analysis. Statistical significance amongst groups was determined using 1-way ANOVA or Student's un-paired T-tests (two-sided), as indicated in the figure legends, and was considered significant when p<0.05. For ELISA data, a paired T-test was used to compare endpoint dilutions for the same sera against DENV and ZIKV antigens. The data were validated to meet the test assumptions (i.e. normal distribution, similar variance between groups).

Example 2

Model of ZIKV Infection in Mice

We characterized ZIKV infection in female C57BL/6 mice using the ZIKV strain H/PF/2013 [Baronti, C. et al. *Genome Announc* 2: e00500-14 (2014)] to determine if immune-competent mice would experience replicating ZIKV infection. After intra-peritoneal infection of mice with ZIKV, virus could be detected within 24 h in the cells of the peritoneum (FIG. 1*a*) and in lymphoid tissues, including the spleen (FIG. 1*b*) and the mesenteric and iliac lymph nodes (FIG. 1*c-d*). Infection persisted beyond 7 days at the site of infection and in lymphoid tissues of immune-competent mice (FIG. 1*a-d*). Concurrent with the infection and clearance of virus, we observed splenic swelling, consistent with an inflammatory response (FIG. 1*e*). However, in adult mice, we did not detect any ZIKV in the brain (FIG. 1*f*), which is consistent with our understanding that ZIKV causes only a mild febrile illness in the majority of adult human patients[1]. Our data showing that ZIKV could be detected at the site of infection and in lymphoid tissues for at least 1 week supported that ZIKV infection persists long enough in immune-competent mice to allow assessment of its influence on foetal development during pregnancy.

Example 3

Figure 2:
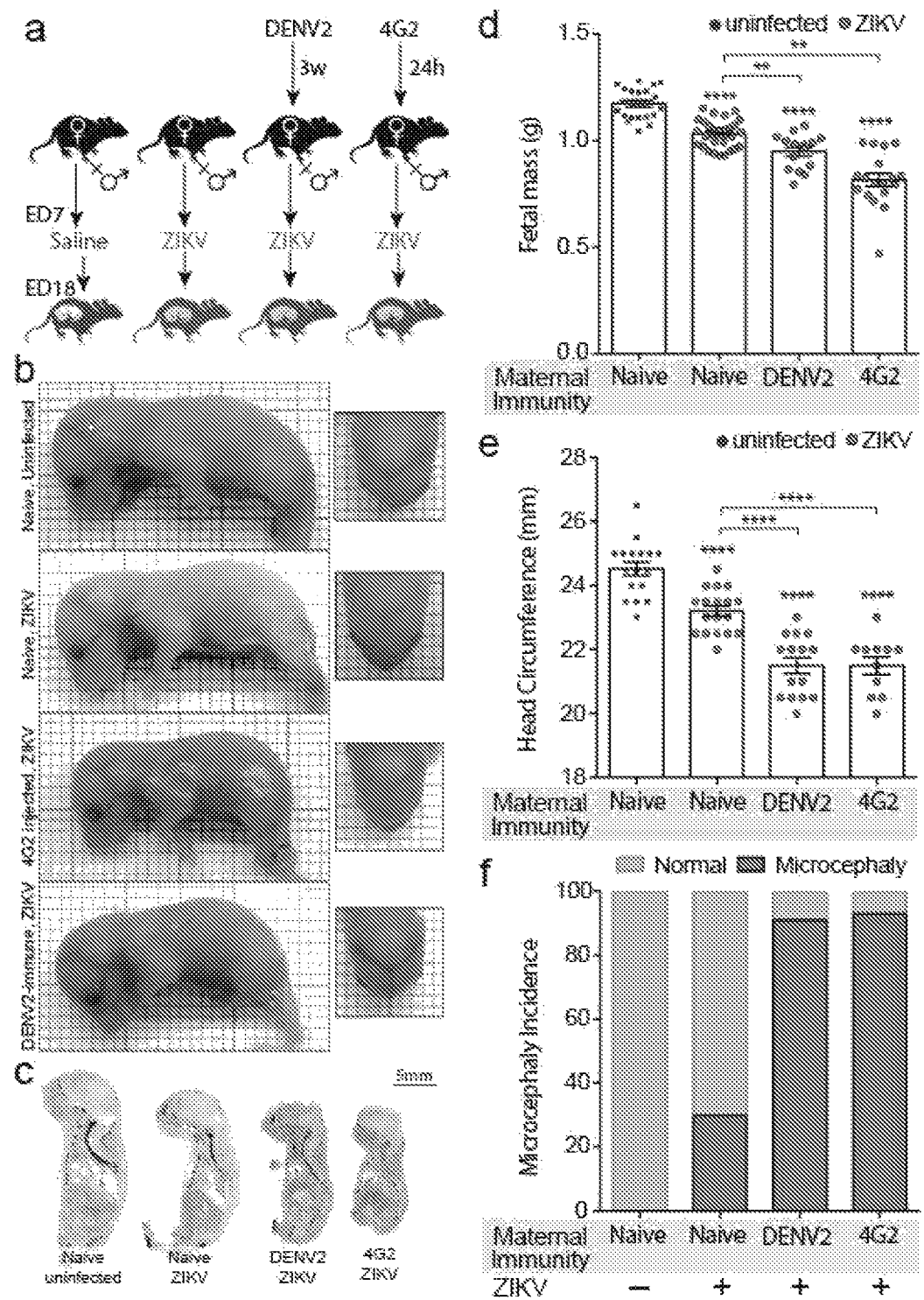
FIG. 2 shows that maternal DENV immunity increases ZIKV-microcephaly in foetuses. (a) Schematic of the experimental time course showing that female naïve mice or mice that were infected with DENV three weeks prior or mice that were adoptively transferred the monoclonal antibody 4G2 (50 µg, i.p.) were each crossed to male mice. Mother mice were infected on E7 after conception and the foetal development was assessed on E18. (b) Representative images of foetal mice on a 1-mm$^2$ grid are provided to show that the DENV2-immune and 4G2-injected groups were visually smaller than controls. (c) Cross-sections of embryos stained with toluidine blue to reveal the reduced size of foetuses of DENV2-immune and 4G2-injected mothers. (d) Mass and (e) head circumference of foetal mice on E18. (f) The incidence of mice having microcephaly, defined as a head size in the 3$^{rd}$ percentile or less, calculated from the standard deviation of foetuses from naïve mothers without ZIKV infection. For panels d-e,  $p<0.01$ and ** $p<0.0001$, by 1-way ANOVA with Holm-Sidak's multiple comparison test. Error bars represent the SEM. Variances do not differ significantly. For d, N=22 (naïve-uninfected), N=28 (naïve-ZIKV), N=15 (DENV2-ZIKV), N=18 (4G2-ZIKV). Fore, N=17 (naïve-uninfected), N=18 (naïve-ZIKV), N=15 (DENV2-ZIKV), N=11 (4G2-ZIKV). Groups contain the combined data from 3 independent experiments.
Figure 3:
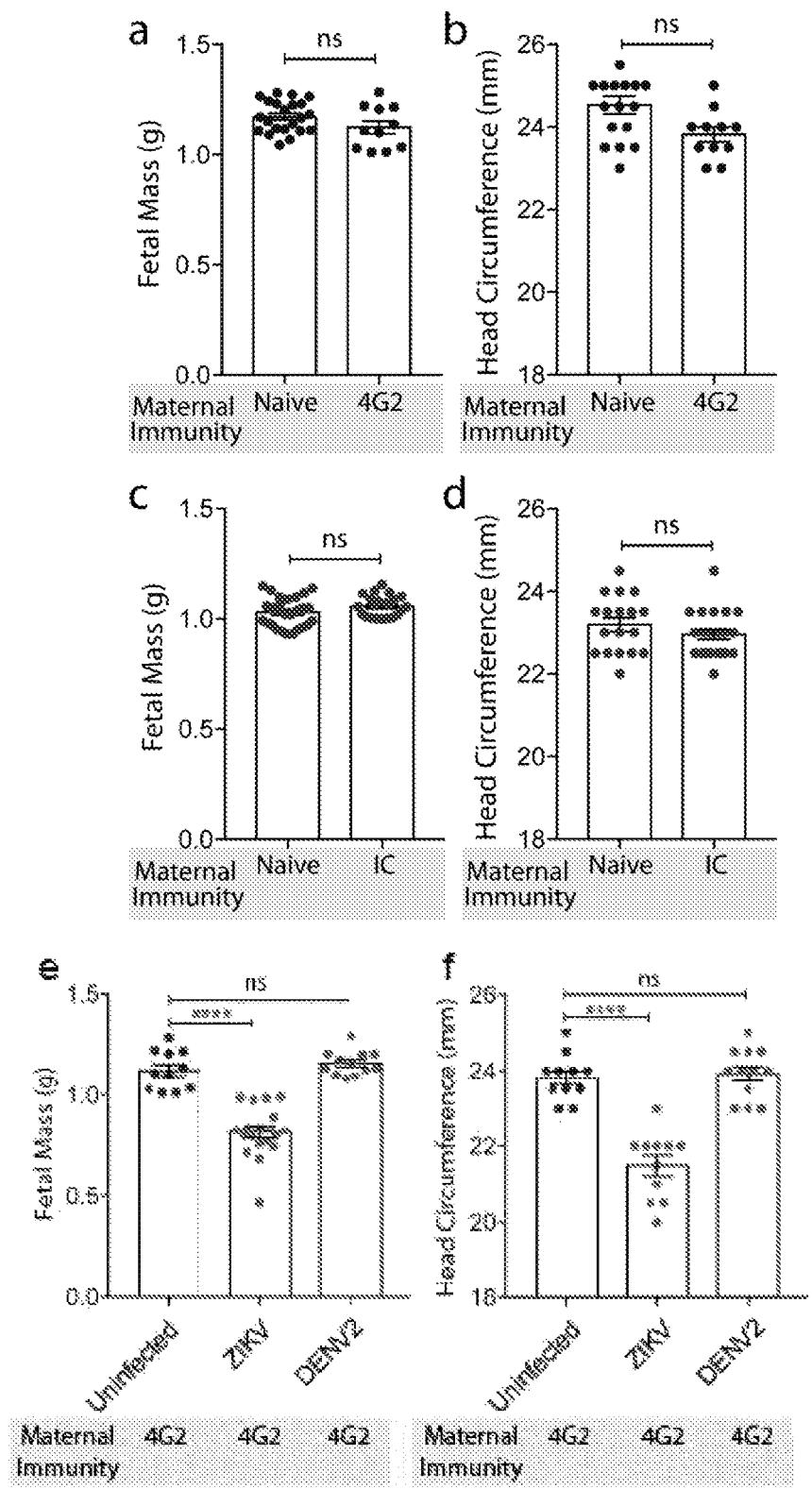
FIG. 3 shows that additional control groups demonstrate the requirement of cross-reactive antibodies and ZIKV for enhanced microcephaly. (a) Foetal mass and (b) head circumference of E18 foetal mice of naïve or 4G2-injected mothers that were uninfected. 4G2 injection of mothers before pregnancy does not cause congenital defects. Error bars represent the SEM and the differences between groups were not significant (ns) by Student's unpaired T-test. (c) Foetal mass and (d) head circumference of E18 foetal mice of naïve and isotype control (IC)-injected mothers that were given ZIKV infection on E7. Differences between naïve and IC-injected mice were ns by Student's unpaired T-test. (e) Foetal mass and (f) head circumference of E18 foetal mice of DENV2-immune mothers infected with DENV2 compared to experimental groups. DENV2 re-infection did not cause differences in foetal mass or head circumference by 1-way ANOVA with Holm-Sidak's multiple comparison test.

Effect of Maternal DENV Immunity on Pathogenesis of DENV and ZIKV Relating to Foetus Size To address the question of whether maternal DENV immunity could enhance embryonic neural complications, we infected mice of varying flavivirus-immune status during pregnancy at embryonic day (E)-7 with ZIKV (FIG. 2*a*). This day was chosen due to its equivalence to the first trimester of foetal development in humans. Mother mice were either naïve (to both ZIKV and DENV), immune to DENV2 after clearing infection, or adoptively transferred monoclonal antibody 4G2, which was raised against DENV2 but is flavivirus cross-reactive [Johnson, A. J., et al. *J Clin Microbiol* 38: 1827-1831 (2000)]. Adoptive transfer of 4G2 was used to identify the contributions of pre-existing cross-reactive antibodies alone (as a component of immunity) to ZIKV pathogenesis. At E18, near full-term, mother mice were killed and the foetal mice were examined. A gross analysis of the foetuses showed that mice that were previously infected with DENV had pups with stunted growth (FIG. 2*b-c*). Quantification of the foetal mass showed a significant decrease in the mass of foetuses of naïve, ZIKV-infected mothers, compared to those of naïve, uninfected controls (FIG. 2*d*). This reduced body size was consistent with previous reports of ZIKV infection in mice [Miner, J. J. et al. *Cell* 165: 1081-1091, (2016)]. However, infected DENV2-immune and 4G2-injected mothers had foetuses that were even smaller than the naïve ZIKV-infected mothers (FIG. 2*b-d*). When examining the circumference of the foetal head, the primary measure used to define microcephaly in humans, naïve ZIKV-infected mothers had foetuses with slightly but significantly smaller heads compared to healthy controls (FIG. 2*e*). However, 4G2-injected and DENV2-immune mothers that were infected with ZIKV had foetuses with head sizes that were substantially smaller than both naïve uninfected mice and naïve ZIKV-infected mice (FIG. 2*e*). Additional control experiments were also performed, showing that no abnormalities were observed after control injection of 4G2 prior to pregnancy without maternal ZIKV infection and isotype control antibodies did not influence foetal size or head circumference in ZIKV-infected mothers (FIG. 3*a-d*). Furthermore, DENV-immune mother mice have normal pups without any reported foetal abnormalities and we did not observe any reduction in foetal size when 4G2-injected mothers were given a challenge of DENV2 rather than ZIKV at E7 (FIG. 3*e-f*), supporting the specificity of the phenotype to ZIKV infection. Next, we looked at the frequency of microcephaly in these foetuses (defined as a head size in the 3rd percentile or less for normal foetuses) and noted that while 30% of foetuses from naïve mice infected at E7 with ZIKV could be assessed as having microcephaly, >90% of the foetuses of DENV2-immune or 4G2-injected mother mice qualified as having microcephaly (FIG. 2*f*). This supports that maternal immunity or flavivirus cross-reactive antibodies can enhance the severity and incidence of microcephaly during ZIKV infection.

Example 4

Figure 5:
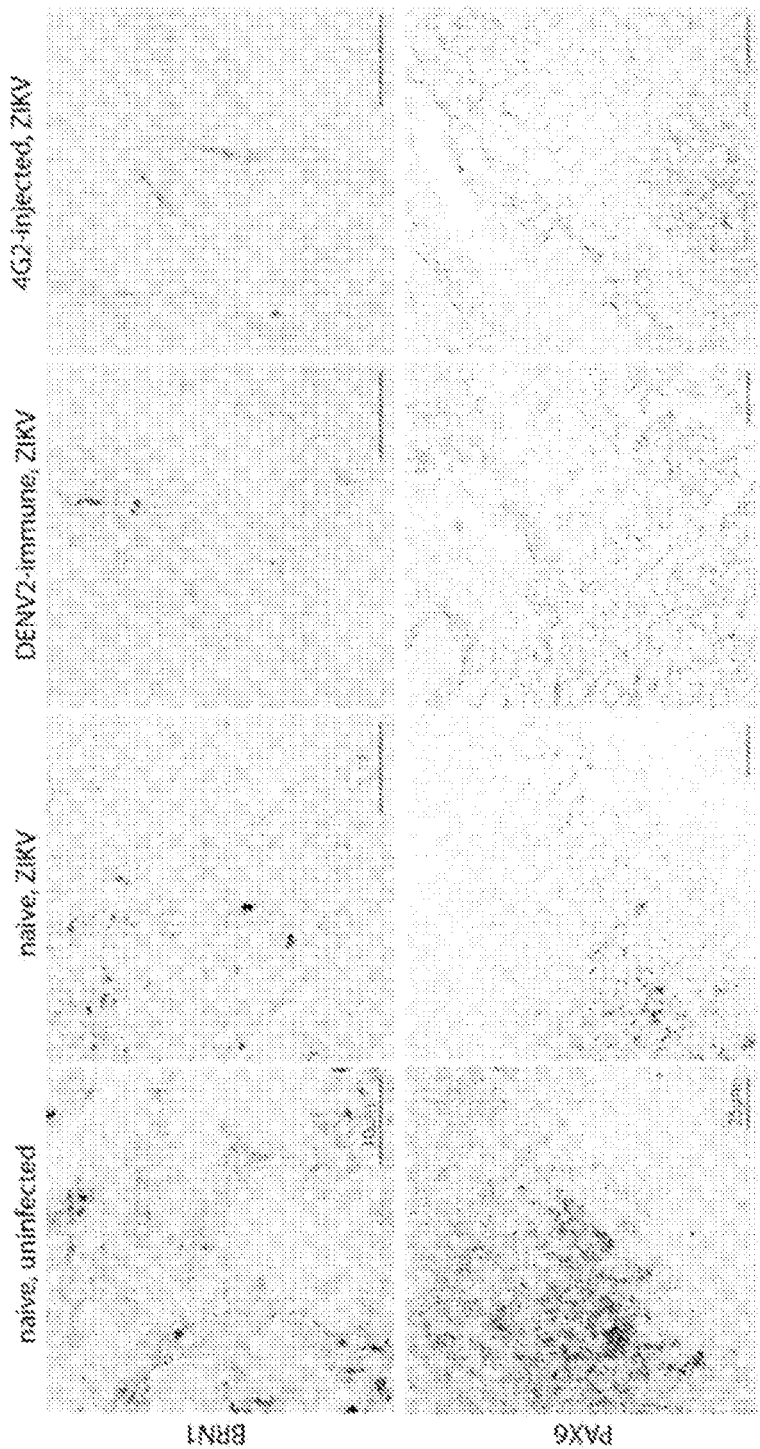
FIG. 5 shows confirmation of protein-level reduction of BRN1 and PAX6 in foetal brains during maternal ZIKV infection. Images of brain sections stained by immunohistochemistry with antibodies against transcription factors BRN1 (40×-magnification) or PAX6 (20×-magnfication). BRN1 is shown at higher magnification since the staining was difficult to visualize at lower magnification. Staining for both transcription factors shows similar trends at the protein level to the mRNA expression data in FIG. 4c, with reduced staining in the foetuses of DENV-naïve ZIKV-infected mothers, with a further reduction in DENV-immune groups.

Effect of Maternal DENV Immunity on Pathogenesis of DENV and ZIKV Relating to Foetal Brain Development To further characterise the impact of ZIKV infection, with and without maternal antibodies, on the development of the foetal brain, we examined the brains by histology (FIG. 4a). The DENV2-immune group showed profound reduction in cortical thickness and loss of integrity of the expected cortical layers (FIG. 4a). In particular, there appeared to be reductions in the size of the ventricular zone, intermediate zone and cortical plate compared to foetuses from naïve uninfected mothers and naïve ZIKV-infected mothers (FIG. 4a). Quantification of cortical thickness from multiple litters showed that these reductions were significant and consistent for foetuses with both DENV2-immune and 4G2-injected mothers compared to foetuses of naïve uninfected mothers and naïve ZIKV-infected mothers (FIG. 4b). The cortical thickness was also moderately reduced in the foetuses of naïve ZIKV infected mothers compared to foetuses of healthy controls (FIG. 4b), although the cortical layers were intact and discernable (FIG. 4a). The transcription factor Brain 1 (Brn1) is used as a marker of cortical development in mice [Sugitani, Y. et al. *Genes Dev* 16: 1760-1765, (2002)]; thus, we measured levels of Brn1 in the brains of E18 embryos from all groups. We observed that levels of Brn1 mRNA were reduced in foetuses from DENV2-immune or 4G2-injected mothers (FIG. 4c), which was correlated with the impaired cortical thickness. We also measured levels of additional genes associated with early cortical neurogenesis, including fork-head box G1 (Foxg1), empty spiracles homologue 2 (Emx2) and Paired box 6 (Pax6). Expression of these genes allows differentiation and proliferation of ventricular zone progenitors as well as expansion of the sub-ventricular zone [Muzio, L. & Mallamaci, A. *J Neurosci* 25: 4435-4441, (2005); Muzio, L. et al. *Nat Neurosci* 5: 737-745, (2002)]. ZIKV infection resulted in reduced expression of both Pax6 and Foxg1, suggesting early brain development was stunted due to ZIKV infection, although Emx2 was not significantly influenced (FIG. 4c). Brain 2 (Brn2) and orthodenticle homeobox protein family genes, Otx1 and Otx2, along with Brn1, aid the differentiation and migration of neurons [McEvilly, R. J., et al. *Science* 295: 1528-1532, (2002)] as well as development of neuronal layers in the cortex and cerebellum [Frantz, G. D., et al. *J Neurosci* 14: 5725-5740 (1994)]. ZIKV infection also suppressed the expression of both Brn2 and Otx family genes. For Pax6, Brn1, and Brn2, foetuses of DENV-immune mothers showed greater deficits than those of naïve mothers (FIG. 4). Suppressed levels of selected cortical markers were verified at the protein level by immunohistochemistry (FIG. 5). Together these results show visually striking and quantifiable defects in the development of the cerebral cortex during ZIKV infection, supported by evidence that cerebral cortex-associated transcription factors are reduced in the foetuses of DENV2-immune mothers.

Example 5

Effect of Maternal DENV Immunity on Foetal DENV and ZIKV Infection

Figure 6:
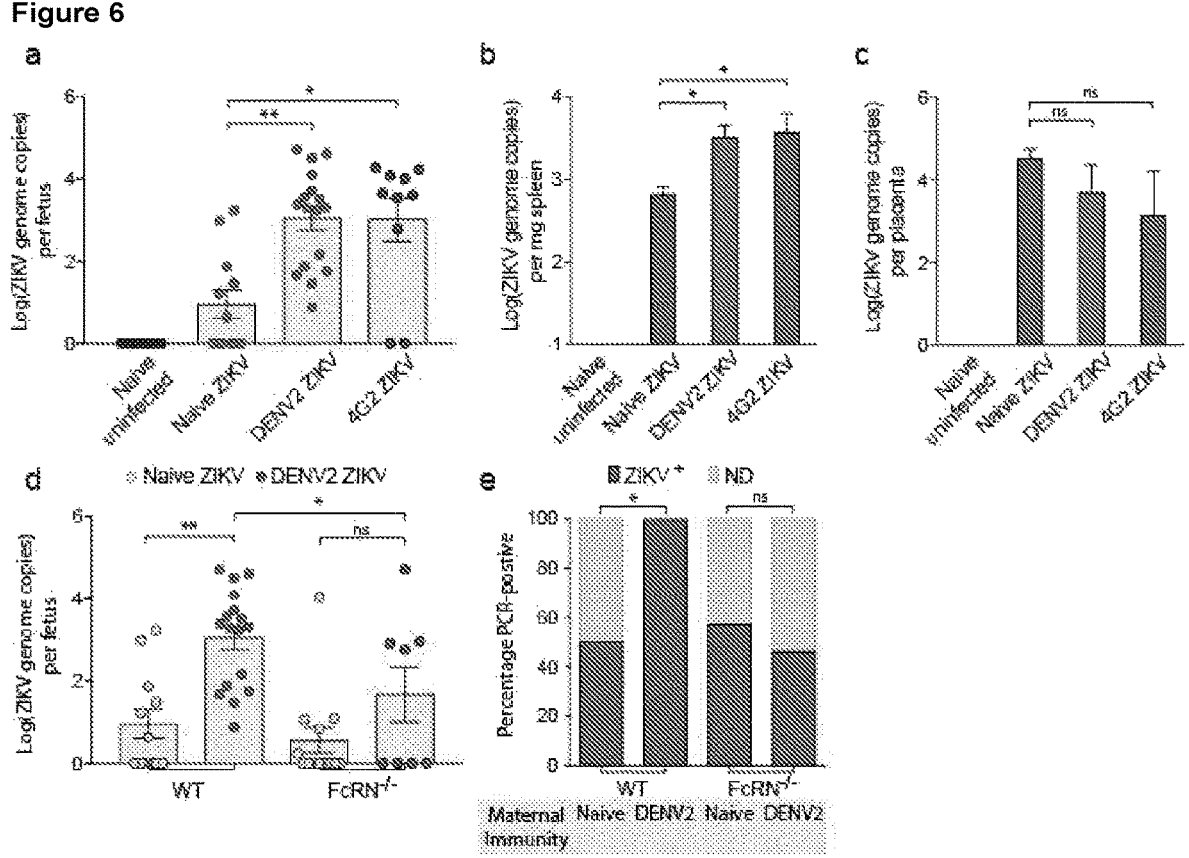
FIG. 6 shows enhanced ZIKV infection of foetuses in DENV-immune mothers. (a) Real time RT-PCR was used to quantify the ZIKV genome copies in the mouse foetuses of DENV-naïve uninfected mothers (n=10), from DENV-naïve ZIKV-infected mothers (n=12), from DENV2-immune ZIKV-infected mothers (n=17), and from 4G2-injected ZIKV-infected mothers (n=10) derived from 2-3 independent experiments. Foetuses were harvested on E10, 3d after maternal infection or E18, 11d after maternal infection for RNA isolation. Foetuses from DENV2-immune and 4G2-injected mothers showed significant increases in ZIKV compared to those of naïve mothers by 1-way ANOVA with Holm-Sidak's multiple comparison test (* indicates $p<0.01$, ** $p<0.001$). (b) Quantification of ZIKV infection in the spleen of mother mice 3d after infection when the foetuses were harvested at E10 (n=3 per group). Error bars represent the SEM. (c) Quantification of ZIKV infection in the placentas at E10. (d) Quantification of ZIKV in DENV-immune (n=17) or -naïve (n=10) WT and DENV-immune (n=8) or -naïve FcRN$^{-/-}$ (n=13) embryos on E10. (e) Proportions of PCR-positive embryos for each group in d. Significance was determined by Fisher's exact test; * indicates $p<0.05$).
Figure 7:
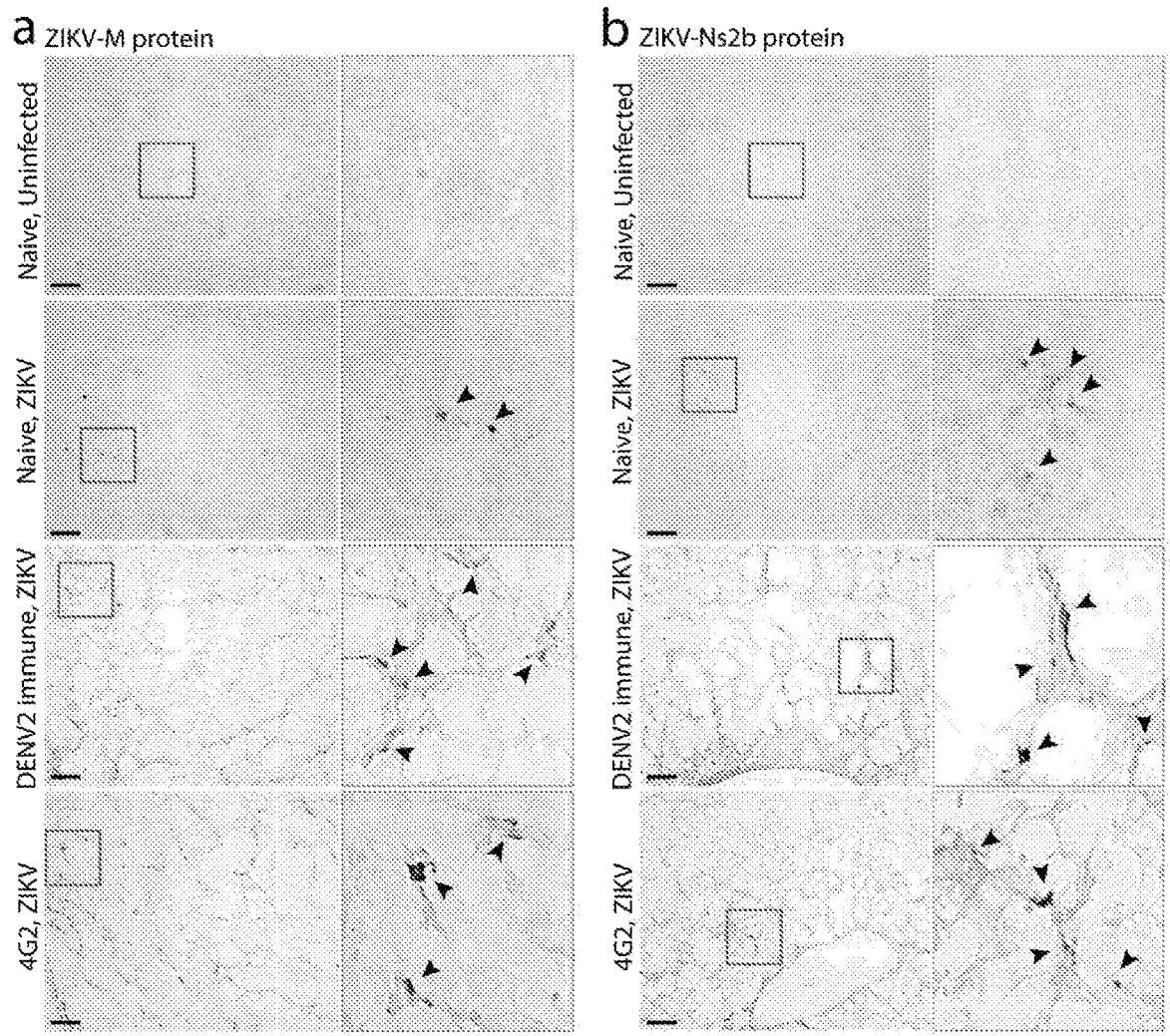
FIG. 7 shows ZIKV antigens detected in the E18 foetal cortex. Foetal brain sections were stained with antibodies against either (a) ZIKV M-protein or (b) ZIKV Ns2b. Both proteins were detected in low amounts in cortex of foetuses from ZIKV-infected mothers, indicating that infection had occurred in the brain and that ZIKV antigen persisted to E18. Images were taken at 20×-magnification. Right panels contain the enlarged area from the boxed region, where arrows indicate cells staining positive for ZIKV proteins. Scale bar=10 μm.

Based on the findings in Example 4 and the potential of the antibody 4G2, which is DENV-directed but ZIKV cross-reactive, to cause enhanced microcephaly in the foetuses of ZIKV-infected mothers, we tested whether antibodies might promote increased translocation of ZIKV into the foetus. We quantified ZIKV genome copies in the foetuses on E10, 3 days after the mother mice had been infected. Surprisingly our results showed that maternal antibody to DENV or monoclonal antibody 4G2 each enhanced infection of the embryo compared to ZIKV infection of naïve mothers (FIG. 6a). ZIKV was detectable in approximately 50% of the embryos of naïve, ZIKV-infected mothers at E10 but 100% of the embryos of DENV2-immune and 80% of 4G2-injected mothers (FIG. 6a). Interestingly, by E18, although brain development was impaired (FIG. 4), ZIKV was undetectable in the brains of all foetuses by PCR; however, immunohistochemistry staining of E18 brain sections for ZIKV proteins NS2b and M showed positive staining, indicating that antigen persisted in the cortex (FIG. 7). DENV-immunity also enhanced the replication of ZIKV in the mother's spleen, consistent with other reports that DENV antibodies can cause ADE we confirmed that this can occur in vivo (FIG. 6b). The viral burden also did not differ in pregnant mice compared to non-pregnant mice (not shown). In contrast to the mother's spleen, prior DENV immunity did not significantly enhance the viral burden in the placenta at E10 (FIG. 6c).

Example 6

Effect of Maternal DENV Immunity on Maternal DENV and ZIKV Viral Load

Figure 8:
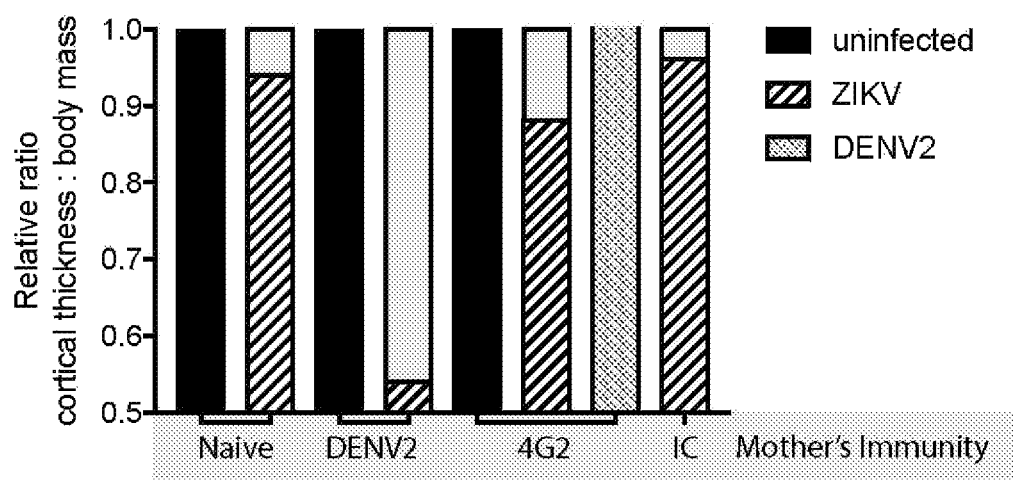
FIG. 8 shows normalized ratio of cortical thickness to body mass for foetal mice. The cortical thickness was normalized to body mass. All ZIKV-infected groups showed disproportionate narrowing of the cerebral cortex even relative to their reduced size, with foetuses of DENV2-immune mothers showing the strongest phenotype.

There are multiple possibilities for how antibodies could enhance translocation of virus into the foetus, including active transport of ZIKV in the form of antibody-bound complexes across the placenta or, alternatively, higher titres in the mother might make trans-placental infection more likely through a different mechanism. Interestingly, the viral load in the mother's spleen did not correlate with the amount of virus in the embryo, since naïve-ZIKV infected mother mice had less than 1-log reduction in viral burden in their spleens compared to DENV2-immune mice, but very low levels of ZIKV were detected in their foetuses or none at all (FIG. 6a-b). This suggests that other factors, besides maternal viral titres alone, could be at play in inducing microcephaly. Indeed, although 4G2-treated mice showed the lowest E18 mass (FIG. 2d), DENV2 immunity resulted in the greatest impairment of brain development at E18 (FIG. 4) and highest foetal viral load at E10 (FIG. 6a). Even so, the foetuses of DENV-immune and 4G2-injected mice showed a greater relative reduction of cortical thickness to body mass compared to those from naïve ZIKV infected mothers (FIG. 8). This, combined with evidence of tissue damage and loss of cortical layers (FIG. 4a), supports a genuine microcephaly phenotype. Thus, overall foetal size may reflect the enhanced infection in the mother, potentially due to intrauterine growth restriction, without necessarily producing the most severe neurological phenotype in the foetus. In contrast, severity of foetal microcephaly appears to be linked to increased ZIKV replication in the foetus in the presence of maternal antibody (FIG. 6a).

Since antibodies are translocated into the foetus with a mechanism dependent on FcRN, we examined whether FcRN contributes to foetal ZIKV infection in DENV-immune mice. We compared viral titres in foetuses of both naïve and DENV2-immune mothers in FcRN$^{-/-}$ mice to wild-type controls. Overall, foetuses of DENV2-immune FcRN$^{-/-}$ mice showed reduced viral titres at E10 compared to the foetuses of wild-type mice (FIG. 6d). Furthermore, ZIKV titres were not significantly higher in the foetuses of DENV2-immune mothers compared to naïve mothers (FIG. 6d), in contrast to the significant enhancement of ZIKV titres observed in the context of DENV2 maternal immunity in wild-type animals (FIG. 6a). In FcRN$^{-/-}$ DENV-immune mothers, only 50% of the foetal mice showed ZIKV infection, compared to 100% of the foetuses of WT DENV-immune mother mice (FIG. 6e). This proportion was significantly lower than the proportion of infected foetuses in WT mice and not significantly different from ZIKV-infected naïve WT or naïve FcRN$^{-/-}$ mice (FIG. 6e) and suggests that FcRN-mediated translocation of immune complexes increases the likelihood of vertical transmission. The foetuses of wild-type mothers that were DENV2-immune showed higher levels of ZIKV than naïve animals after ZIKV infection, suggesting that DENV2-antibodies also result in enhanced levels of ZIKV if the foetus becomes infected by a mechanism independent of FcRN. These results support both ADE and FcRN-mediated immune complex translocation into the foetus can contribute to enhanced ZIKV infection in foetal mice.

Example 7

Blockade of FcRN Limits ZIKV Transcytosis

To establish that FcRN blockade could inhibit transcytosis of ZIKV immune complexes by human endothelial cells, we used another method involving a trans-well system. A schematic of the trans-well system is shown in FIG. 12a. Endothelial cells expressing FcRN (HULEC-5A) were grown on trans-well inserts to form a tight monolayer, while trophoblast cells (HTR-8/SVneo), which are infection targets, were grown on the bottom of the well, on the other side of the trans-well. Either ZIKV alone or ZIKV immune-complexed with the flavivirus-cross-reactive antibody 4G2 were added to the top chamber of the trans-well and the infection levels of trophoblast cells were monitored after 24 h to determine if various concentrations of 4G2 enhanced virus infection in this system compared to the levels of infection due to diffusion alone. Furthermore, another group was pre-treated with an antibody against FcRN to determine if the infection levels of trophoblast cells could be reduced by blocking FcRN-mediated translocation (FIG. 12a). First, it was determined that neither ZIKV alone nor ZIKV-antibody complexes (at multiple concentrations of antibody 4G2) enhanced permeability of the HULEC-5A monolayers (FIG. 12b). When the soluble dye FITC-dextran was applied to the top chamber and measured in the bottom chamber, there was not a significant increase in dye leakage observed in ZIKV-treated groups over the control groups suggesting that a tight monolayer formed and diffusion was minimal. In contrast, an antibody concentration dependent enhancement of ZIKV infection was observed in target cells on the opposite site of the monolayer, suggesting that antibodies enhanced the translocation of the virus across the monolayer. Anti-FcRN antibodies significantly blocked the translocation of virus-immune complexes and limited infection of trophoblast cells in the bottom chamber (FIG. 12c). These results support that blockade of FcRN can limit transcytosis of immune complexes by human cells. Multiple antibodies that bind to ZIKV and FcRN enhance the uptake of ZIKV-antibody complexes by cells that express FcRN. Furthermore, multiple reagents that block FcRN-mediated transport of antibodies block uptake and translocation of ZIKV across cell monolayers.

Figure 13:
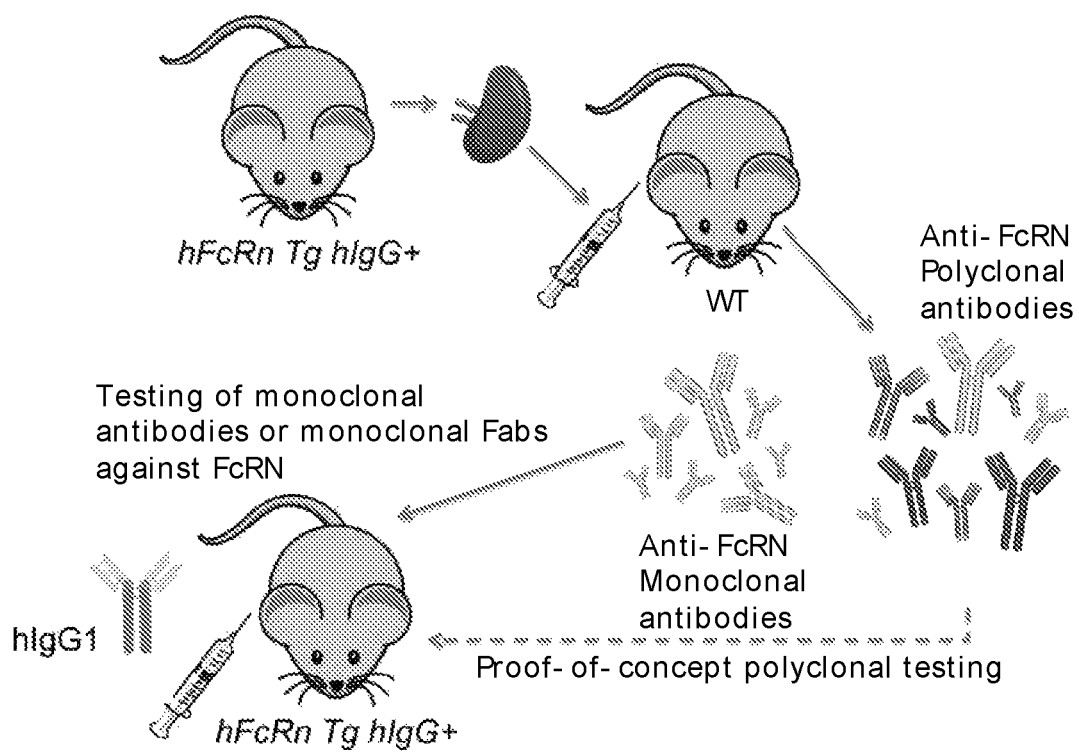
FIG. 13 shows that antibodies are raised against the human FcRN protein by immunizing wild-type mice with tissue from mice expressing human FcRN (or purified hFcRN protein).

Therapeutic antibodies are raised against human FcRN protein by immunizing wild-type mice with tissue from mice expressing human FcRN (or purified hFcRN protein) and isolating serum from those mice (FIG. 13). This generates a polyclonal serum against human FcRN that is effective in preventing transcytosis of immune complexes (of human IgG and ZIKA) in either humans or mice expressing the human FcRN receptor. Monoclonal antibodies that have the ability to block FcRN can be identified from this polyclonal serum using known techniques. Both polyclonal serum and some monoclonal antibodies produced from B cells that are derived from FcRN-immunized animals have a neutralizing effect on FcRN and prevent transcytosis of virus-immune complexes. The efficacy of blocking antibodies is tested using transgenic mice that express human FcRN (FIG. 13) or in cell culture using cells expressing human FcRN (FIG. 12a) to identify FcRN-neutralizing antibodies. Similarly, modified antibodies, such as Fabs (Fragment antigen binding, after pepsin digest, etc) retain their activity and block FcRN and ZIKV transcytosis in vivo.

SUMMARY

Here, using a model where maternal infection occurs at time points of mouse foetal development corresponding to the first trimester of pregnancy in humans, we show that maternal antibodies enhance trans-placental infection of mouse foetuses which leads to exacerbated microcephaly. This involves reduced cortical thickness, substantial loss of certain cortical layers and impaired induction of transcriptional profiles key for brain development. Infection was undetectable by PCR in E18 foetal brains while the signs of damage to the cortex and ZIKV antigens remained. Head size alone did not indicate the full severity of reduced cortical thickness in mice, neither could this be interpreted from the mother's viral burden, although ADE in the mothers could be seen in terms of higher ZIKV burden in DENV-immune compared to naïve pregnant mice. Our results also indicate that FcRN mediates a significant amount of the antibody-enhanced effects of disease since FcRN$^{-/-}$ animals have reduced proportions of the embryonic mice infected with ZIKV in utero. This is likely due to the essential role of FcRN in mediating transcytosis of immune complexes across the placenta from mother to foetus [Roopenian, D. C. et al. *J Immunol* 170: 3528-3533 (2003)].

Figure 9:
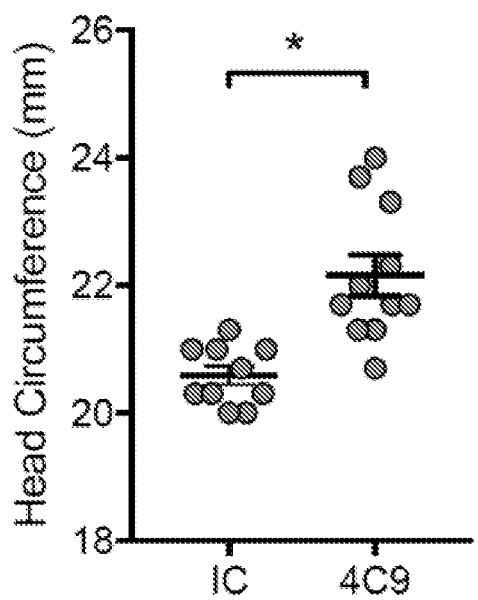
FIG. 9 shows that blocking antibodies against FcRN reduce severity of ZIKV-induced microcephaly in foetuses of DENV-immune mothers. Blocking antibody against FcRN (clone 4C9) or isotype control (IC) antibodies were injected therapeutically into DENV-immune pregnant mother mice prior to ZIKV infection on E7. Head circumference of the foetal mice was measured on E18. Head circumferences were significantly increased in 4C9 treated foetal mice compared to those given IC, $p<0.0001$.

Based on these data, showing that FcRN-deficient mothers have fewer foetuses that develop ZIKV infection than wild-type mothers (with functional FcRN), we proposed that targeting the FcRN receptor with a monoclonal blocking antibody would be an efficient way to prevent translocation of the virus into the foetus. We used a blocking and neutralizing antibody against FcRN (clone 4C9, which targets the light chain of rat FcRN, but the heavy chain of human FcRN) to treat DENV-immune pregnant mice prior to ZIKV infection. The results indicate that 4C9 is effective in limiting microcephaly in the foetuses of DENV-immune mothers (FIG. 9). Foetuses born to 4C9-treated DENV-immune mothers have significantly larger head circumference compared to foetuses born to DENV-immune mothers who are given isotype control antibodies as a mock treatment (FIG. 9). These results demonstrate that we have reduced to practice that therapeutic targeting of FcRN prevents or reduces severity of microcephaly.

Any listing or discussion of an apparently prior-published document in this specification should not necessarily be taken as an acknowledgement that such document is part of the state of the art or is common general knowledge.

REFERENCES

Baronti, C. et al. Complete coding sequence of zika virus from a French polynesia outbreak in 2013. *Genome Announc* 2, doi:10.1128/genomeA.00500-14 (2014).

Berger, M., McCallus, D. E. & Lin, C. S. Rapid and reversible responses to IVIG in autoimmune neuromuscular diseases suggest mechanisms of action involving competition with functionally important autoantibodies. *J Peripher Nerv Syst* 18, 275-296, doi:10.1111/jns5.12048 (2013).

Cauchemez, S. et al. Association between Zika virus and microcephaly in French Polynesia, 2013-15: a retrospective study. *Lancet* 387, 2125-2132, doi:10.1016/50140-6736(16)00651-6 (2016).

Christianson, G. J. et al. Monoclonal antibodies directed against human FcRn and their applications. *MAbs* 4, 208-216, doi:10.4161/mabs.4.2.19397 (2012).

Cole et al., *Monoclonal Antibodies and Cancer Therapy* Alan R. Liss, Inc., pp 77-96 (1985).

Cote, R. J. et al. Generation of human monoclonal antibodies reactive with cellular antigens. *Proc Natl Acad Sci USA* 80, 2026-2030 (1983).

Dejnirattisai, W. et al. Dengue virus sero-cross-reactivity drives antibody-dependent enhancement of infection with zika virus. *Nat Immunol*, 17(9):1102-8, doi:10.1038/ni.3515 (2016).

Frantz, G. D., Weimann, J. M., Levin, M. E. & McConnell, S. K. OW and Otx2 define layers and regions in developing cerebral cortex and cerebellum. *J Neurosci* 14, 5725-5740 (1994).

Johnson, A. J., Martin, D. A., Karabatsos, N. & Roehrig, J. T. Detection of anti-arboviral immunoglobulin G by using a monoclonal antibody-based capture enzyme-linked immunosorbent assay. *J Clin Microbiol* 38, 1827-1831 (2000).

Kenanova, V. et al. Tailoring the pharmacokinetics and positron emission tomography imaging properties of anti-carcinoembryonic antigen single-chain Fv-Fc antibody fragments. *Cancer Res* 65, 622-631 (2005).

Kohler, G. & Milstein, C. Continuous cultures of fused cells secreting antibody of predefined specificity. 1975. *J Immunol* 174, 2453-2455 (2005).

Lanciotti, R. S. et al. Genetic and serologic properties of Zika virus associated with an epidemic, Yap State, Micronesia, 2007. *Emerg Infect Dis* 14, 1232-1239, doi: 10.3201/eid1408.080287 (2008).

Mezo, A. R. et al. Reduction of IgG in nonhuman primates by a peptide antagonist of the neonatal Fc receptor FcRn. *Proc Natl Acad Sci USA* 105, 2337-2342, doi:10.1073/pnas.0708960105 (2008).

McEvilly, R. J., de Diaz, M. O., Schonemann, M. D., Hooshmand, F. & Rosenfeld, M. G. Transcriptional regulation of cortical neuron migration by POU domain factors. *Science* 295, 1528-1532, doi:10.1126/science.1067132 (2002).

Miner, J. J. et al. Zika Virus Infection during Pregnancy in Mice Causes Placental Damage and Fetal Demise. *Cell* 165, 1081-1091, doi:10.1016/j.cell.2016.05.008 (2016).

Mlakar, J. et al. Zika Virus Associated with Microcephaly. *N Engl J Med* 374, 951-958, doi:10.1056/NEJMoa1600651 (2016).

Morrison, S. L., Johnson, M. J., Herzenberg, L. A. & Oi, V. T. Chimeric human antibody molecules: mouse antigen-binding domains with human constant region domains. *Proc Natl Acad Sci USA* 81, 6851-6855 (1984).

Musso, D. & Gubler, D. J. Zika Virus. *Clin Microbiol Rev* 29, 487-524, doi:10.1128/CMR.00072-15 (2016).

Muzio, L. & Mallamaci, A. Foxg1 confines Cajal-Retzius neuronogenesis and hippocampal morphogenesis to the dorsomedial pallium. *J Neurosci* 25, 4435-4441, doi: 10.1523/JNEUROSCI.4804-04.2005 (2005).

Muzio, L. et al. Conversion of cerebral cortex into basal ganglia in Emx2(−/−) Pax6(Sey/Sey) double-mutant mice. *Nat Neurosci* 5, 737-745, doi:10.1038/nn892 (2002).

Qiu, Y., Lv, W., Xu, M. & Xu, Y. Single chain antibody fragments with pH dependent binding to FcRn enabled prolonged circulation of therapeutic peptide in vivo. *J Control Release* 229, 37-47, doi:10.1016/j.jconrel.2016.03.017 (2016).

Raghavan, M., Chen, M. Y., Gastinel, L. N. & Bjorkman, P. J. Investigation of the interaction between the class I MHC-related Fc receptor and its immunoglobulin G ligand. *Immunity* 1, 303-315 (1994).

Roopenian, D. C. et al. The MHC class 1-like IgG receptor controls perinatal IgG transport, IgG homeostasis, and fate of IgG-Fc-coupled drugs. *J Immunol* 170, 3528-3533 (2003).

Roopenian, D. C. & Akilesh, S. FcRn: the neonatal Fc receptor comes of age. *Nat Rev Immunol* 7, 715-725, doi:10.1038/nri2155 (2007).

Seijsing, J. et al. An engineered affibody molecule with pH-dependent binding to FcRn mediates extended circulatory half-life of a fusion protein. *Proc Natl Acad Sci USA* 111, 17110-17115, doi:10.1073/pnas.1417717111 (2014).

Sesarman, A., Vidarsson, G. & Sitaru, C. The neonatal Fc receptor as therapeutic target in IgG-mediated autoimmune diseases. *Cell Mol Life Sci* 67, 2533-2550, doi: 10.1007/s00018-010-0318-6 (2010).

Sockolosky, J. T., Kivimae, S. & Szoka, F. C. Fusion of a short peptide that binds immunoglobulin G to a recombinant protein substantially increases its plasma half-life in mice. *PLoS One* 9, e102566, doi:10.1371/journal.pone.0102566 (2014).

Sugitani, Y. et al. Brn-1 and Brn-2 share crucial roles in the production and positioning of mouse neocortical neurons. *Genes Dev* 16, 1760-1765, doi:10.1101/gad.978002 (2002).

Wang, Z., Fraley, C. & Mezo, A. R. Discovery and structure-activity relationships of small molecules that block the human immunoglobulin G-human neonatal Fc receptor (hIgG-hFcRn) protein-protein interaction. *Bioorg Med Chem Lett* 23, 1253-1256, doi:10.1016/j.bmcl.2013.01.014 (2013).

Wu, K. Y. et al. Vertical transmission of Zika virus targeting the radial glial cells affects cortex development of offspring mice. *Cell Res* 26, 645-654, doi:10.1038/cr.2016.58 (2016).

The invention claimed is:

1. A method of treatment to reduce vertical transmission of virus infection from a DENV-immune mother to a foetus, comprising administering to the mother an efficacious amount of an isolated reagent that blocks the maternal Fc neonatal receptor (FcRN) activity, wherein the isolated reagent is an antibody or antigen-binding fragment thereof comprising monoclonal mouse, human, humanized or chimeric antibody or fragment thereof; and the virus infection is a Zika virus infection, thereby reducing vertical transmission of virus infection from the mother to its developing foetus and the incidence of microcephaly in the foetus compared to if the mother is untreated.

2. The method of claim 1, wherein the antibody is 4C9 (hybridoma ATCC deposit number CRL-2437) or a humanized or chimeric antibody form or fragment thereof.

3. The method of claim 1, wherein the mother and foetus are human.

4. The method of claim 1, wherein the antibody or antigen-binding fragment thereof binds with specificity to the heavy chain of FcRN.

5. The method of claim 1, wherein the isolated reagent is IgG or IgY.

6. The method of claim 4, wherein the antibody or antigen-binding fragment thereof binds with specificity to a FcRN peptide sequence comprising GEEFMNFDLKQGT (SEQ ID NO: 3).

\* \* \* \* \*

SEQUENCE LISTING

```
<160> NUMBER OF SEQ ID NOS: 22

<210> SEQ ID NO 1
<211> LENGTH: 1433
<212> TYPE: DNA
<213> ORGANISM: Homo sapiens
<220> FEATURE:
<221> NAME/KEY: misc_feature
```

<223> OTHER INFORMATION: human FcRn nucleotide sequence

<400> SEQUENCE: 1

```
acaggatgtg agagaggaac tggggtctcc agtcacggga gccaggagcc ggccagggcc      60
gcaggcagga agggagcgag gctgaaggga acgtcgtcct ctcagcatgg gggtcccgcg     120
gcctcagccc tgggcgctgg ggctcctgct ctttctcctt cctgggagcc tgggcgcaga     180
aagccacctc tccctcctgt accaccttac cgcggtgtcc tcgcctgccc cggggactcc     240
tgccttctgg gtgtccggct ggctgggccc gcagcagtac ctgagctaca atagcctgcg     300
gggcgaggcg gagccctgtg gagcttgggt ctgggaaaac caggtgtcct ggtattggga     360
gaaagagacc acagatctga ggatcaagga gaagctcttt ctggaagctt tcaaagcttt     420
ggggggaaaa ggtccctaca ctctgcaggg cctgctgggc tgtgaactgg ccctgacaa      480
cacctcggtg cccaccgcca agttcgccct gaacggcgag gagttcatga atttcgacct     540
caagcagggc acctgggggt gggactggcc cgaggccctg ctatcagtc agcggtggca     600
gcagcaggac aaggcggcca acaaggagct caccttcctg ctattctcct gcccgcaccg     660
cctgcgggag cacctggaga ggggccgcgg aaacctggag tggaaggagc cccctccat      720
gcgcctgaag gcccgaccca gcagccctgg cttttccgtg cttacctgca gcgccttctc     780
cttctaccct ccggagctgc aacttcggtt cctgcggaat gggctggccg ctggcaccgg     840
ccagggtgac ttcggcccca cagtgacgg atccttccac gcctcgtcgt cactaacagt     900
caaaagtggc gatgagcacc actactgctg cattgtgcag cacgcggggc tggcgcagcc     960
cctcagggtg gagctggaat ctccagccaa gtcctccgtg ctcgtggtgg aatcgtcat    1020
cggtgtcttg ctactcacgg cagcggctgt aggaggagct ctgttgtgga aaggatgag    1080
gagtgggctg ccagccccctt ggatctccct tcgtggagac gacaccgggg tcctcctgcc    1140
caccccaggg gaggcccagg atgctgattt gaaggatgta aatgtgattc agccaccgc    1200
ctgaccatcc gccattccga ctgctaaaag cgaatgtagt caggcccctt tcatgctgtg    1260
agacctcctg gaacactggc atctctgagc ctccagaagg ggttctgggc ctagttgtcc    1320
tccctctgga gccccgtcct gtggtctgcc tcagtttccc ctcctaatac atatggctgt    1380
tttccacctc gataatataa cacgagtttg ggcccaaaaa aaaaaaaaaa aaa           1433
```

<210> SEQ ID NO 2
<211> LENGTH: 365
<212> TYPE: PRT
<213> ORGANISM: Homo sapiens
<220> FEATURE:
<221> NAME/KEY: misc_feature
<223> OTHER INFORMATION: human FcRN amino acid sequence

<400> SEQUENCE: 2

```
Met Gly Val Pro Arg Pro Gln Pro Trp Ala Leu Gly Leu Leu Leu Phe
1               5                   10                  15

Leu Leu Pro Gly Ser Leu Gly Ala Glu Ser His Leu Ser Leu Leu Tyr
            20                  25                  30

His Leu Thr Ala Val Ser Ser Pro Ala Pro Gly Thr Pro Ala Phe Trp
        35                  40                  45

Val Ser Gly Trp Leu Gly Pro Gln Gln Tyr Leu Ser Tyr Asn Ser Leu
    50                  55                  60

Arg Gly Glu Ala Glu Pro Cys Gly Ala Trp Val Trp Glu Asn Gln Val
65                  70                  75                  80

Ser Trp Tyr Trp Glu Lys Glu Thr Thr Asp Leu Arg Ile Lys Glu Lys
```

```
                    85                  90                  95
Leu Phe Leu Glu Ala Phe Lys Ala Leu Gly Gly Lys Gly Pro Tyr Thr
                100                 105                 110

Leu Gln Gly Leu Leu Gly Cys Glu Leu Gly Pro Asp Asn Thr Ser Val
            115                 120                 125

Pro Thr Ala Lys Phe Ala Leu Asn Gly Glu Glu Phe Met Asn Phe Asp
        130                 135                 140

Leu Lys Gln Gly Thr Trp Gly Gly Asp Trp Pro Glu Ala Leu Ala Ile
145                 150                 155                 160

Ser Gln Arg Trp Gln Gln Gln Asp Lys Ala Ala Asn Lys Glu Leu Thr
                165                 170                 175

Phe Leu Leu Phe Ser Cys Pro His Arg Leu Arg Glu His Leu Glu Arg
                180                 185                 190

Gly Arg Gly Asn Leu Glu Trp Lys Glu Pro Pro Ser Met Arg Leu Lys
            195                 200                 205

Ala Arg Pro Ser Ser Pro Gly Phe Ser Val Leu Thr Cys Ser Ala Phe
        210                 215                 220

Ser Phe Tyr Pro Pro Glu Leu Gln Leu Arg Phe Leu Arg Asn Gly Leu
225                 230                 235                 240

Ala Ala Gly Thr Gly Gln Gly Asp Phe Gly Pro Asn Ser Asp Gly Ser
                245                 250                 255

Phe His Ala Ser Ser Ser Leu Thr Val Lys Ser Gly Asp Glu His His
                260                 265                 270

Tyr Cys Cys Ile Val Gln His Ala Gly Leu Ala Gln Pro Leu Arg Val
            275                 280                 285

Glu Leu Glu Ser Pro Ala Lys Ser Ser Val Leu Val Val Gly Ile Val
        290                 295                 300

Ile Gly Val Leu Leu Leu Thr Ala Ala Ala Val Gly Gly Ala Leu Leu
305                 310                 315                 320

Trp Arg Arg Met Arg Ser Gly Leu Pro Ala Pro Trp Ile Ser Leu Arg
                325                 330                 335

Gly Asp Asp Thr Gly Val Leu Leu Pro Thr Pro Gly Glu Ala Gln Asp
                340                 345                 350

Ala Asp Leu Lys Asp Val Asn Val Ile Pro Ala Thr Ala
            355                 360                 365

<210> SEQ ID NO 3
<211> LENGTH: 13
<212> TYPE: PRT
<213> ORGANISM: Homo sapiens
<220> FEATURE:
<221> NAME/KEY: misc_feature
<223> OTHER INFORMATION: human FcRN peptide sequence

<400> SEQUENCE: 3

Gly Glu Glu Phe Met Asn Phe Asp Leu Lys Gln Gly Thr
1               5                   10

<210> SEQ ID NO 4
<211> LENGTH: 17
<212> TYPE: DNA
<213> ORGANISM: Artificial Sequence
<220> FEATURE:
<223> OTHER INFORMATION: ZIKV-specific forward primer
<220> FEATURE:
<221> NAME/KEY: misc_feature
<223> OTHER INFORMATION: validated ZIKA virus-specific forward primer

<400> SEQUENCE: 4
```

```
ccgctgccca acacaag                                                        17

<210> SEQ ID NO 5
<211> LENGTH: 24
<212> TYPE: DNA
<213> ORGANISM: Artificial Sequence
<220> FEATURE:
<223> OTHER INFORMATION: ZIKV-specific reverse primer
<220> FEATURE:
<221> NAME/KEY: misc_feature
<223> OTHER INFORMATION: validated ZIKA virus-specific reverse primer

<400> SEQUENCE: 5
ccactaacgt tcttttgcag acat                                                24

<210> SEQ ID NO 6
<211> LENGTH: 31
<212> TYPE: DNA
<213> ORGANISM: Artificial Sequence
<220> FEATURE:
<223> OTHER INFORMATION: FAM-probe

<400> SEQUENCE: 6
agcctacctt gacaagcagt cagacactca a                                        31

<210> SEQ ID NO 7
<211> LENGTH: 18
<212> TYPE: DNA
<213> ORGANISM: Artificial Sequence
<220> FEATURE:
<223> OTHER INFORMATION: Mouse Brn1 forward primer

<400> SEQUENCE: 7
ctcggcgcag gaaatcac                                                       18

<210> SEQ ID NO 8
<211> LENGTH: 17
<212> TYPE: DNA
<213> ORGANISM: Artificial Sequence
<220> FEATURE:
<223> OTHER INFORMATION: Mouse Brn1 reverse primer

<400> SEQUENCE: 8
cccgcacgac ctccttt                                                        17

<210> SEQ ID NO 9
<211> LENGTH: 20
<212> TYPE: DNA
<213> ORGANISM: Artificial Sequence
<220> FEATURE:
<223> OTHER INFORMATION: Mouse Brn2 forward primer

<400> SEQUENCE: 9
ccatttcctc aaatgcccta                                                     20

<210> SEQ ID NO 10
<211> LENGTH: 20
<212> TYPE: DNA
<213> ORGANISM: Artificial Sequence
<220> FEATURE:
<223> OTHER INFORMATION: Mouse Brn2 reverse primer

<400> SEQUENCE: 10
ggaggggtca tccttttctc                                                     20
```

```
<210> SEQ ID NO 11
<211> LENGTH: 20
<212> TYPE: DNA
<213> ORGANISM: Artificial Sequence
<220> FEATURE:
<223> OTHER INFORMATION: Mouse Otx1 forward primer

<400> SEQUENCE: 11
aagacaagcc actccgacaa                                                 20

<210> SEQ ID NO 12
<211> LENGTH: 20
<212> TYPE: DNA
<213> ORGANISM: Artificial Sequence
<220> FEATURE:
<223> OTHER INFORMATION: Mouse Otx1 reverse primer

<400> SEQUENCE: 12
gcgaagtcct tcaagctgtt                                                 20

<210> SEQ ID NO 13
<211> LENGTH: 20
<212> TYPE: DNA
<213> ORGANISM: Artificial Sequence
<220> FEATURE:
<223> OTHER INFORMATION: Mouse Otx2 forward primer

<400> SEQUENCE: 13
ggaagaggtg gcactgaaaa                                                 20

<210> SEQ ID NO 14
<211> LENGTH: 20
<212> TYPE: DNA
<213> ORGANISM: Artificial Sequence
<220> FEATURE:
<223> OTHER INFORMATION: Mouse Otx2 reverse primer

<400> SEQUENCE: 14
ctgacctcca ttctgctgct                                                 20

<210> SEQ ID NO 15
<211> LENGTH: 20
<212> TYPE: DNA
<213> ORGANISM: Artificial Sequence
<220> FEATURE:
<223> OTHER INFORMATION: Mouse Emx2 forward primer

<400> SEQUENCE: 15
accttctacc cctggctcat                                                 20

<210> SEQ ID NO 16
<211> LENGTH: 19
<212> TYPE: DNA
<213> ORGANISM: Artificial Sequence
<220> FEATURE:
<223> OTHER INFORMATION: Mouse Emx2 reverse primer

<400> SEQUENCE: 16
gaatccgctt tggctttct                                                  19

<210> SEQ ID NO 17
<211> LENGTH: 20
<212> TYPE: DNA
<213> ORGANISM: Artificial Sequence
<220> FEATURE:
<223> OTHER INFORMATION: Mouse Pax6 forward primer
```

```
<400> SEQUENCE: 17
ctaaggatgt tgaacgggca                                               20

<210> SEQ ID NO 18
<211> LENGTH: 20
<212> TYPE: DNA
<213> ORGANISM: Artificial Sequence
<220> FEATURE:
<223> OTHER INFORMATION: Mouse Pax6 reverse primer

<400> SEQUENCE: 18
agttggtgtt ctctccccct                                               20

<210> SEQ ID NO 19
<211> LENGTH: 19
<212> TYPE: DNA
<213> ORGANISM: Artificial Sequence
<220> FEATURE:
<223> OTHER INFORMATION: Mouse Foxg1 forward primer

<400> SEQUENCE: 19
tggaaggcct ccacagaac                                                19

<210> SEQ ID NO 20
<211> LENGTH: 18
<212> TYPE: DNA
<213> ORGANISM: Artificial Sequence
<220> FEATURE:
<223> OTHER INFORMATION: Mouse Foxg1 reverse primer

<400> SEQUENCE: 20
tggcaaggca tgtagcaa                                                 18

<210> SEQ ID NO 21
<211> LENGTH: 19
<212> TYPE: DNA
<213> ORGANISM: Artificial Sequence
<220> FEATURE:
<223> OTHER INFORMATION: Mouse actin forward primer

<400> SEQUENCE: 21
cgtcgacaac ggctccggc                                                19

<210> SEQ ID NO 22
<211> LENGTH: 29
<212> TYPE: DNA
<213> ORGANISM: Artificial Sequence
<220> FEATURE:
<223> OTHER INFORMATION: Mouse actin reverse primer

<400> SEQUENCE: 22
ggtgttgaag gtctcaaaca tgatctggg                                     29
```